(12) United States Patent (10) Patent No.: US 8,734,364 B1
Mantzaris et al. (45) Date of Patent: May 27, 2014

(54) DEVICE AND METHOD FOR OBTAINING A BIOLOGICAL SAMPLE

(71) Applicant: Genetic Technologies Limited, Victoria (AU)

(72) Inventors: Debbie Mantzaris, Victoria (AU); Nicola Charlotte Andrews, Victoria (AU); Denis Greco, Victoria (AU); David Jonathan Sparling, Queensland (AU)

(73) Assignee: Genetic Technologies Limited (AU)

( * ) Notice: Subject to any disclaimer, the term of this patent is extended or adjusted under 35 U.S.C. 154(b) by 0 days.

(21) Appl. No.: 14/074,215

(22) Filed: Nov. 7, 2013

(51) Int. Cl.
*A61B 5/00* (2006.01)

(52) U.S. Cl.
USPC ............................................ 600/572

(58) Field of Classification Search
USPC ................. 600/564–567, 569–572
See application file for complete search history.

(56) References Cited

U.S. PATENT DOCUMENTS

| | | | |
|---|---|---|---|
| 3,877,464 A | 4/1975 | Vermes | |
| 3,995,636 A | 12/1976 | Murray et al. | |
| 4,194,513 A | 3/1980 | Rhine et al. | |
| 4,675,286 A | 6/1987 | Calenoff | |
| 4,681,123 A | 7/1987 | Valtchev | |
| 4,866,806 A | 9/1989 | Bedford | |
| 4,988,617 A | 1/1991 | Landegren et al. | |
| 5,106,377 A | 4/1992 | Martin | |
| 5,242,794 A | 9/1993 | Whiteley et al. | |
| 5,494,810 A | 2/1996 | Barany et al. | |
| 5,916,175 A * | 6/1999 | Bauer | 600/567 |
| 5,954,670 A * | 9/1999 | Baker | 600/567 |
| 6,059,735 A | 5/2000 | Sgro | |
| 6,346,086 B1 | 2/2002 | Maksem et al. | |
| 6,582,938 B1 | 6/2003 | Su et al. | |
| 6,610,005 B1 * | 8/2003 | Tao | 600/34 |
| 6,749,576 B2 * | 6/2004 | Bauer | 600/567 |
| 6,969,585 B2 | 11/2005 | Lorincz et al. | |
| 7,087,028 B2 * | 8/2006 | Sak | 600/569 |

(Continued)

FOREIGN PATENT DOCUMENTS

| | | |
|---|---|---|
| CN | 2134162 | 5/1993 |
| CN | 201171680 | 12/2008 |
| EP | 0363196 | 4/1990 |
| GB | 2126100 | 3/1984 |

OTHER PUBLICATIONS

International Search Report prepared by the Australian Patent Office on Mar. 31, 2010 for International Application No. PCT/AU2010/000071.

(Continued)

*Primary Examiner* — Max Hindenburg
(74) *Attorney, Agent, or Firm* — Sheridan Ross P.C.

(57) ABSTRACT

Embodiments relate generally to a sampling device adapted for sampling of biological materials from a subject and methods of use or manufacture of such devices, as well as diagnostic methods employing such devices and kits including such devices. The sampling device may comprise: an outer tube; an elongate insertion member having a first end and a second end, wherein the first end is distal of the second end, the insertion member being received in and sized to be movable through the outer tube; a coupling portion disposed at the first end of the insertion member; and a sampling portion coupled to the coupling portion and configured to collect the biological materials. The coupling portion is separable from the insertion member.

18 Claims, 15 Drawing Sheets

(56) References Cited

U.S. PATENT DOCUMENTS

| | | | |
|---|---|---|---|
| 7,767,448 B2* | 8/2010 | Yong | 435/309.1 |
| 8,343,072 B2* | 1/2013 | Bacon et al. | 600/567 |
| 8,591,563 B2 | 11/2013 | Karpiel et al. | |
| 2003/0227611 A1 | 12/2003 | Fein et al. | |
| 2004/0126796 A1 | 7/2004 | Carlson et al. | |
| 2012/0122091 A1 | 5/2012 | Vom et al. | |

OTHER PUBLICATIONS

Written Opinion prepared by the Australian Patent Office on Mar. 31, 2010 for International Application No. PCT/AU2010/000071.
Official Action for U.S. Appl. No. 14/066,264 mailed Jan. 28, 2014, 9 pages.
Official Action for U.S. Appl. No. 13/146,376 mailed Jan. 28, 2014, 9 pages.
Adinolfi et al., "First trimester prenatal diagnosis using transcervical cells: an evaluation," Human Reproduction Update, 1997, vol. 3, No. 4, pp. 383-392.
Al-Mufti et al., "Investigation of Maternal Blood Enriched for Fetal Cells: Role in Screening and Diagnosis of Fetal Trisomies," Am. J. Med. Genet., 1999, vol. 85, pp. 66-75.
Bauer et al., "Paternity testing after pregnancy termination using laser microdissection of chorionic villi," Int. J. Legal Med., 2002, vol. 116, pp. 39-42.
Bischoff et al., "Endocervical fetal trophoblast for prenatal genetic diagnosis," Current Opinion in Obstetrics Gynecology, 2006, vol. 18, pp. 216-220.
Bulmer et al., "Immunohistochemical Characterization of Cells Retrieved by Transcervical Sampling in Early Pregnancy," Prenatal Diag., 1995, vol. 15, pp. 1143-1153.
Bussani et al., "Prenatal Diagnosis of Common Aneuploidies in Transcervical Samples Using Quantitative Fluorescent-PCR Analysis," Molecular Diagnosis & Therapy, 2007, vol. 11, Iss. 2, pp. 117-121.
Bussani et al., "Strategies for the isolation and detection of fetal cells in transcervical samples," Prenatal Diag., 2002, vol. 22, pp. 1098-1101.
Bussani et al., "Use of the Quantitative Fluorescent-PCR Assay in the Study of Fetal DNA from Micromanipulated Transcervical Samples," Mol. Diagn., 2004, vol. 8, pp. 259-263.
Cioni et al., "Fetal cells in cervical mucus in the first trimester of pregnancy," Prenatal Diag., 2003, vol. 23, pp. 168-171.
Fejgin et al., "Fetal cells in the uterine cervix: a source for early non-invasive prenatal diagnosis," Prenatal Diag., 2001, vol. 21, pp. 619-621.
Findlay et al., "Fluorescent polymerase chain reaction: Part I. A new method allowing genetic diagnosis and DNA fingerprinting of single cells," Hum. Reprod. Update, 1996, vol. 2(2), pp. 137-152.
Findlay et al., "Same day diagnosis of Down's syndrome and sex in single cells using multiplex flourescent PCR," J. Clin. Pathol. Mol. Pathol., 1998, vol. 51, pp. 164-167.
Findlay, I. et al., "Using MF-PCR to diagnose multiple defects from single cells: implications for PGD," Mol. Cell. Endocrin., 2001, vol. 183, pp. S5-S12.
Fitzgerald et al., "PCR Amplification of HIV and Cellular DNA Sequences in Formaldehyde-Fixed, Immunoreactive White Blood Cells," BioTechniques, 1993, vol. 15(1), pp. 128-133.
Goldberg et al., "First-trimester fetal chromosomal diagnosis using endocervical lavage: A negative evaluation," Am. J. Obstet. Gynecol., 1980, vol. 138, pp. 436-440.
Katz-Jaffe et al., "DNA identification of fetal cells isolated from cervical mucus: potential for early non-invasive prenatal diagnosis," BJOG, 2005, vol. 112, pp. 595-600.
Lehmann et al., "Real-Time PCR Analysis of DNA and RNA Extracted from Formalin-Fixed and Paraffin-Embedded Biopsies," Methods, 2001, vol. 25, pp. 409-418.
Mantzaris et al., "Preliminary report: correct diagnosis of sex in fetal cells isolated from cervical mucus during early pregnancy," Aus. NZ J. Obstet. Gynecol., 2005, vol. 45, pp. 529-532.
Massari et al., "Non-invasive early prenatal molecular diagnosis using retrieved transcervical trophoblast cells," Hum. Genet., 1996, vol. 97, pp. 150-155.
Miller et al., "Transcervical recovery of fetal cells from the lower uterine pole: reliability of recovery and histological/immunocytochemical analysis of recovered cell populations," Hum. Reprod., 1999, vol. 14(2), pp. 521-531.
Rhine et al., "A Simple Alternative to Amniocentesis for First Trimester Prenatal Diagnosis," Birth Defects Orig. Article Ser., 1977, vol. 12(3D), pp. 231-247.
Rhine et al., "Prenatal sex detection with endocervical smears: Successful results utilizing Y-body fluorescence," Am. J. Obstet. Gynecol., 1975, vol. 122, pp. 155-160.
Rodeck et al., "Methods for the Transcervical Collection of Fetal Cells During the First Trimester of Pregnancy," Prenatal Diag., 1995, vol. 15, pp. 933-942.
Shettles, "Use of the Y Chromosome in Prenatal Sex Determination," Nature, 1971, vol. 230, No. 5288, pp. 52-53.
Tutschek et al., "Isolation of Fetal Cells from Transcervical Samples by Micromanipulation: Molecular Confirmation of Their Fetal Origin and Diagnosis of Fetal Aneuploidy," Prenatal Diag., 1995, vol. 15, pp. 951-960.
Warren et al., "Prenatal Sex Determination from Exfoliated Cells Found in Cervical Mucosa," Am. J. Hum. Genet., 1972, vol. 24, No. 6, Pt. 1, p. 29a.

* cited by examiner

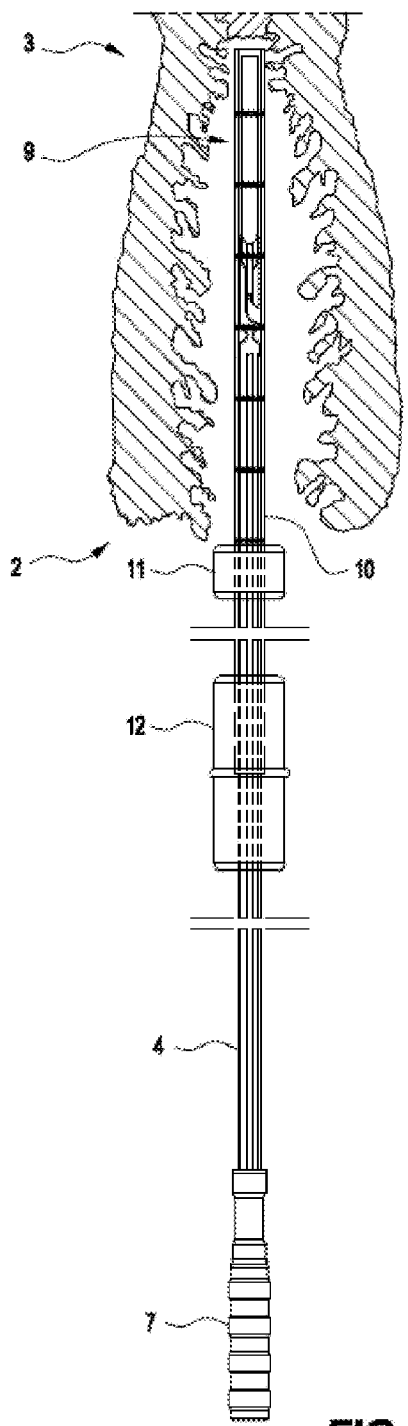 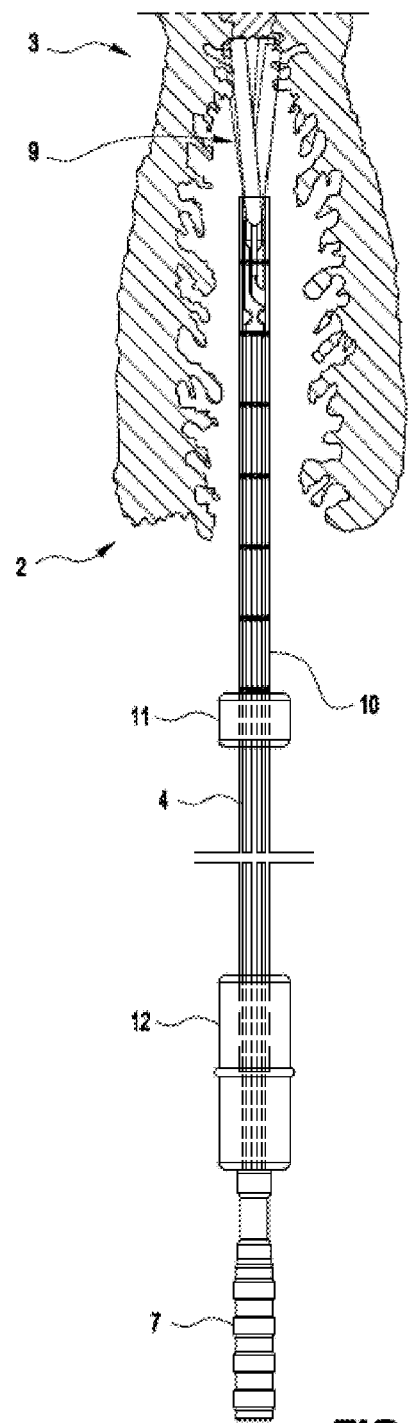
*FIG. 11a*  *FIG. 11b*

DEVICE AND METHOD FOR OBTAINING A BIOLOGICAL SAMPLE

TECHNICAL FIELD

Described embodiments generally relate to a device and method for obtaining biological material and in particular, to a device and method for transcervically obtaining biological samples.

BACKGROUND

Early prenatal diagnosis to detect fetal genetic disorders is desirable for both expectant mothers and physicians to make informed decisions. Until recently, non-invasive screening to identify an individual's risk for fetal aneuploidy (predominantly trisomy 21) relied on either maternal serum analytes and/or ultrasonography at gestational weeks 10 to 13 or 16 to 18 weeks (or at both points) with detection rates of 70-96% and a false positive rate of ~5%, depending on the screening method employed. A positive screening result requires a subsequent invasive procedure (amniocentesis or chorionic villus sampling (CVS)) for confirmatory definitive diagnosis, which carries a small, but significant risk of miscarriage and the results are rarely available before 13 weeks of pregnancy because of the time required for cell culture and analysis.

During the past two decades, many laboratories around the world have attempted to develop a non-invasive prenatal test for the diagnosis of chromosomal abnormalities using rare fetal cells present in the maternal circulation. Reliably isolating sufficient fetal cells from maternal blood for genetic testing has proven difficult due to their rarity (one fetal cell per $10^5$-$10^8$ nucleated maternal cells or 1-10 fetal cells per ml of maternal blood), the inefficiency of cell sorting techniques using fetal-cell specific markers, variable levels of maternal contamination, the tendency for fetal deoxyribonucleic acid (DNA) to disintegrate during chromosome extraction and their persistence in the maternal circulation from previous pregnancies. This approach has been abandoned by most groups for the above mentioned reasons.

It was not until 1997 that researchers discovered the existence of cell free fetal DNA (cffDNA) in the maternal circulation which presented a new possible target for non-invasive prenatal testing (NIPT). CffDNA in the maternal circulation is theorized to be derived from placental cells undergoing apoptosis (fetal DNA is cleaved into small 150-200 base pair fragments) and can be detected reliably after the seventh week of gestation. Current prenatal screening programs have now incorporated cffDNA analysis as part of prenatal management for sex determination of sex linked disorders and Rhesus D incompatibility. More recently, cffDNA has been used for aneuploidy testing (Trisomy 21, Trisomy 18, Trisomy 13, and sex chromosome aneuploidies), paternity testing and for the prediction of many pregnancy complications, including preterm birth, pre-eclampsia and fetal growth restriction. However, further research in this area has been hindered by the low concentration of circulatory fetal DNA in the maternal circulation (accounting for 10% of all cell free DNA at 11-13 weeks gestation (interquartile range 7.8-13%), the interference of excessive amounts of maternal DNA in the plasma sample, and the influence of maternal weight on fetal fraction (decreases from 11.7% at 60 kg to 3.9% at 160 kg). If the fetal fraction is below 4%, non-invasive prenatal testing is currently unable to provide a result for aneuploidy testing.

In light of this, and given that cffDNA in the maternal circulation are believed to be derived from apoptotic trophoblast cells it is hypothesized that transcervical samples may provide an alternative and perhaps superior source of both cffDNA and/or fetal cells to samples derived from maternal circulation. Unlike maternal blood in which multiple circulating fetal cell types exist, fetal cells in the transcervical samples are all of placental origin and are overwhelmingly trophoblasts.

It was long assumed that the cervical canal contained trophoblasts of fetal origin. The early embryo is covered with chorion levae, but later in the gestation the chorionic surface is smooth. However, it was not until 1971 that the presence of fetal cells in the endocervix was confirmed by identification of Y-chromosome bearing cells in midcervical mucus samples collected with a cotton swab. Subsequent reports assumed that these fetal cells were shed from the regressing chorionic villous into the lower uterine pole. In this scenario, it is most likely to occur between 7 and 13 weeks gestation, before fusion of the deciduas basalis and parietalis. Desquamated trophoblasts are believed first to accumulate behind the cervical mucus at the level of the internal opening section and then become ensconced in the cervical mucus.

These biologic events thus define the window of opportunity for endocervical sampling to be of use for prenatal diagnoses, although several studies have demonstrated trophoblast recovery as early as 5 weeks gestation.

Efforts to extract trophoblasts were first made in the 1970's. Rhine et al. (1977) described "antenatal cell extractors" that flush the endocervical canal with sterile saline to recover fetal cells. After culture, fetal metaphases from recovered cells were detected in approximately 50% of cases. However, other investigators reported negative results, leading to overall skepticism concerning clinical application. In hindsight, inability to detect fetal cells probably also reflected deficiencies in the clinicians' techniques in obtaining the endocervical specimen, as well as poor sensitivity of methods used to confirm the presence of fetal cells.

Interest was rekindled in the 1990's, several groups since have attempted to isolate fetal cells/DNA from transcervical samples using various sampling techniques including cotton swabs, cytology brushes, aspiration of mucus, and lavage of the endocervical canal or intrauterine cavity with reported detection rates of 24%-96%. Again, however, interest waned in most centres because analysis was difficult. The presumptive fetal cells embedded in mucus were not readily amenable to fluorescent in situ hybridization (FISH). More recently, molecular polymerase chain reaction (PCR) techniques for micromanipulated cell clumps of trophoblastic origin were demonstrated to have utility for transcervical samples.

Most transcervical specimens contain a variety of maternally derived cells (leukocytes, macrophages, squamous epithelia, columnar epithelia, and endocervical cells) as well as different fetal-derived cells (extravillous cytotrophoblasts, intravillous cytotrophoblasts and syncytiotrophoblasts) and free fetal/maternal nuclei. The frequency of each fetal cell type is variable and seemingly dependent on the collection method and gestational age.

It is desired to address or ameliorate one or more shortcomings or disadvantages associated with prior systems for obtaining biological samples, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or a group of elements, integers or steps, but not the exclusion of any other elements, integer or step, or group of elements, integers or steps.

SUMMARY

Some embodiments relate to a sampling device adapted for transcervical sampling of biological materials from a patient comprising:
- an outer tube having visible reference marks at a first end of the tube, the marks indicating intervals of distance along the first end of the tube;
- an elongate insertion member having a first end and a second end, wherein the first end is distal of the second end, the insertion member being received in and sized to be movable through the outer tube;
- a coupling portion disposed at the first end of the insertion member;
- a sampling portion coupled to the coupling portion and configured to collect the biological materials by absorption or adsorption;
- a first stop disposed adjacent the reference marks on the outer tube, the position of the first stop being adjustable with respect to the reference marks on the outer tube; and
- a second stop arranged to restrict the distance that the first end of the insertion member can extend past the first end of the outer tube;
- wherein the first stop is sized to pass through a vagina of the patient but to be restricted from passing through an external os of a cervix of the patient, and wherein the outer tube is sized to pass through the external os; and
- wherein the insertion member is formed to have a structurally weakened portion that is structurally weakened relative to immediately adjacent portions of the insertion member and is formed proximally of the coupling portion at the first end of the insertion member, wherein the structurally weakened portion facilitates separation of the coupling portion from the insertion member; and
- wherein the outer tube and insertion member are movable relative to each other between at least a first position where the sampling portion is covered by the outer tube, a second position where the sampling member is uncovered by the outer tube and the coupling portion is at least partially covered by the outer tube, and a third position where the sampling portion, coupling portion and structurally weakened portion are uncovered by the outer tube to allow separation of the coupling portion from the insertion member.

Some embodiments relate to a sampling device adapted for transcervical sampling of biological materials from a patient comprising:
- an outer tube having visible reference marks at a first end of the tube, the marks indicating intervals of distance along the first end of the tube;
- an elongate insertion member having a first end and a second end, wherein the first end is distal of the second end, the insertion member being received in and sized to be movable through the outer tube;
- a coupling portion disposed at the first end of the insertion member;
- a sampling portion coupled to the coupling portion and configured to collect the biological materials by absorption or adsorption;
- a first stop disposed adjacent the reference marks on the outer tube, the position of the first stop being adjustable with respect to the reference marks on the outer tube; and
- a second stop arranged to restrict the distance that the first end of the insertion member can extend past the first end of the outer tube;
- wherein the first stop is sized to pass through a vagina of the patient but to be restricted from passing through an external os of a cervix of the patient, and wherein the outer tube is sized to pass through the external os; and
- wherein the insertion member is formed to have a structurally weakened portion that is structurally weakened relative to immediately adjacent portions of the insertion member and is formed proximally of the coupling portion at the first end of the insertion member, wherein the structurally weakened portion facilitates separation of the coupling portion from the insertion member.

Some embodiments relate to a method of manufacturing a sampling device adapted for transcervical sampling of biological materials from a patient, the method comprising:
- forming an outer tube;
- forming an elongate insertion member having a coupling portion at a first end and a structurally weakened portion that is structurally weakened relative to immediately adjacent portions of the insertion member and is formed proximally of the coupling portion at the first end of the insertion member,
- forming a first stop and a second stop;
- positioning at a first end of the outer tube the first stop;
- positioning on a second end of the outer tube the second stop;
- inserting the first end of the insertion member through the second end of the outer tube until the coupling member emerges out of the first end of the outer tube; and
- coupling a sampling portion to the coupling member.

The method may further comprise printing on the outer tube a series of markings, and the first stop may be positioned relative to the markings. The second stop member may comprise a central ridge, and the step of assembling on a second end of the outer tube the second stop may comprise inserting the second end of the outer tube into a central lumen of the second stop until an end face of the second end of the outer tube is aligned with the central ridge. The physical interactions between the insertion member, the outer tube, and the second stop may resist the movement of the outer tube to a position where the coupling member is completely exposed, and the application of additional force may be required to completely expose the coupling member.

Some embodiments relate to a kit adapted for transcervical sampling of biological materials from a patient comprising:
- the sampling device of embodiments described and/or claimed herein;
- a severing member actuable to separate the coupling and sampling portions from the insertion member; and
- a transport medium to transport the coupling and sampling portions after they have been severed from the insertion member.

Some embodiments relate to sampling device adapted for sampling of biological materials from a subject comprising:
- an outer tube;
- an elongate insertion member having a first end and a second end, wherein the first end is distal of the second end, the insertion member being received in and sized to be movable through the outer tube;
- a coupling portion disposed at the first end of the insertion member;

a sampling portion coupled to the coupling portion and configured to collect the biological materials;
a first stop disposed on the outer tube; and
a second stop arranged to restrict the distance that the first end of the insertion member can extend past the first end of the outer tube;
wherein the coupling portion is separable from the insertion member; and
wherein the outer tube and insertion member are movable relative to each other between at least a first position where the sampling portion is covered by the outer tube, a second position where the sampling portion is uncovered by the outer tube and the coupling portion is at least partially covered by the outer tube, and a third position where the sampling portion and coupling portion are uncovered by the outer tube to allow separation of the coupling portion from the insertion member.

Some embodiments relate to sampling device adapted for sampling of biological materials from a subject comprising:
an outer tube;
an elongate insertion member having a first end and a second end, wherein the first end is distal of the second end, the insertion member being received in and sized to be movable through the outer tube;
a coupling portion disposed at the first end of the insertion member; and
a sampling portion coupled to the coupling portion and configured to collect the biological materials;
wherein the coupling portion is separable from the insertion member.

Some embodiments relate to a method of obtaining a transcervical biological sample from a patient, comprising the steps of:
adjusting the position of a positioning member on a sampling device based on a cervical length of the patient;
inserting the sampling device through a vagina of the patient until the positioning member contacts an external os of the cervix of the patient;
retracting an outer sleeve of the sampling device until a limiting member of the sampling device contacts a limiting structure of the sampling device;
withdrawing the sampling device from the patient after allowing time for a sample to be collected by the sampling device,
retracting the outer sleeve further to expose a structurally weakened portion of the sampling device;
separating a sampling head of the sampling device from a body of the sampling device at the structurally weakened portion.

Some embodiments relate to a method of obtaining a biological sample from a subject, comprising the steps of:
adjusting the position of a positioning member on a sampling device based on a body passage length of the subject;
inserting the sampling device into the body passage until the positioning member contacts a body structure at an end of the body passage;
retracting an outer sleeve of the sampling device until a limiting member of the sampling device contacts a limiting structure of the sampling device;
withdrawing the sampling device from the subject after allowing time for a sample to be collected by the sampling device,
retracting the outer sleeve further to expose a coupling portion of the sampling device;
separating a sampling head of the sampling device from a body of the sampling device at the coupling portion.

Some embodiments relate to a method of performing diagnosis on a biological sample of a subject, comprising the steps of:
obtaining a biological sample using a sampling device according to embodiments described and/or claimed herein;
processing the sample;
detecting chromosomal abnormalities and/or performing DNA analysis or other tests;
determining whether the sample contains traits of interest and/or abnormalities to determine the existence or likely existence of a condition or a characteristic of the subject or an offspring of the subject.

The condition may be one of pre-eclampsia, preterm labour, a single-gene disorder, an imprinting disorder or a genetic disease, and the characteristic may be one of the sex or paternity of a fetus.

Embodiments are described in further detail below, by way of example and with reference to the accompanying drawings.

BRIEF DESCRIPTION OF THE DRAWINGS

FIG. 11A shows a lengthwise view of the sampling device of FIG. 4 in the first position relative to a human cervix;
FIG. 11B shows a lengthwise view of the sampling device of FIG. 4 in the second position relative to a human cervix.

DETAILED DESCRIPTION

Figure 1:
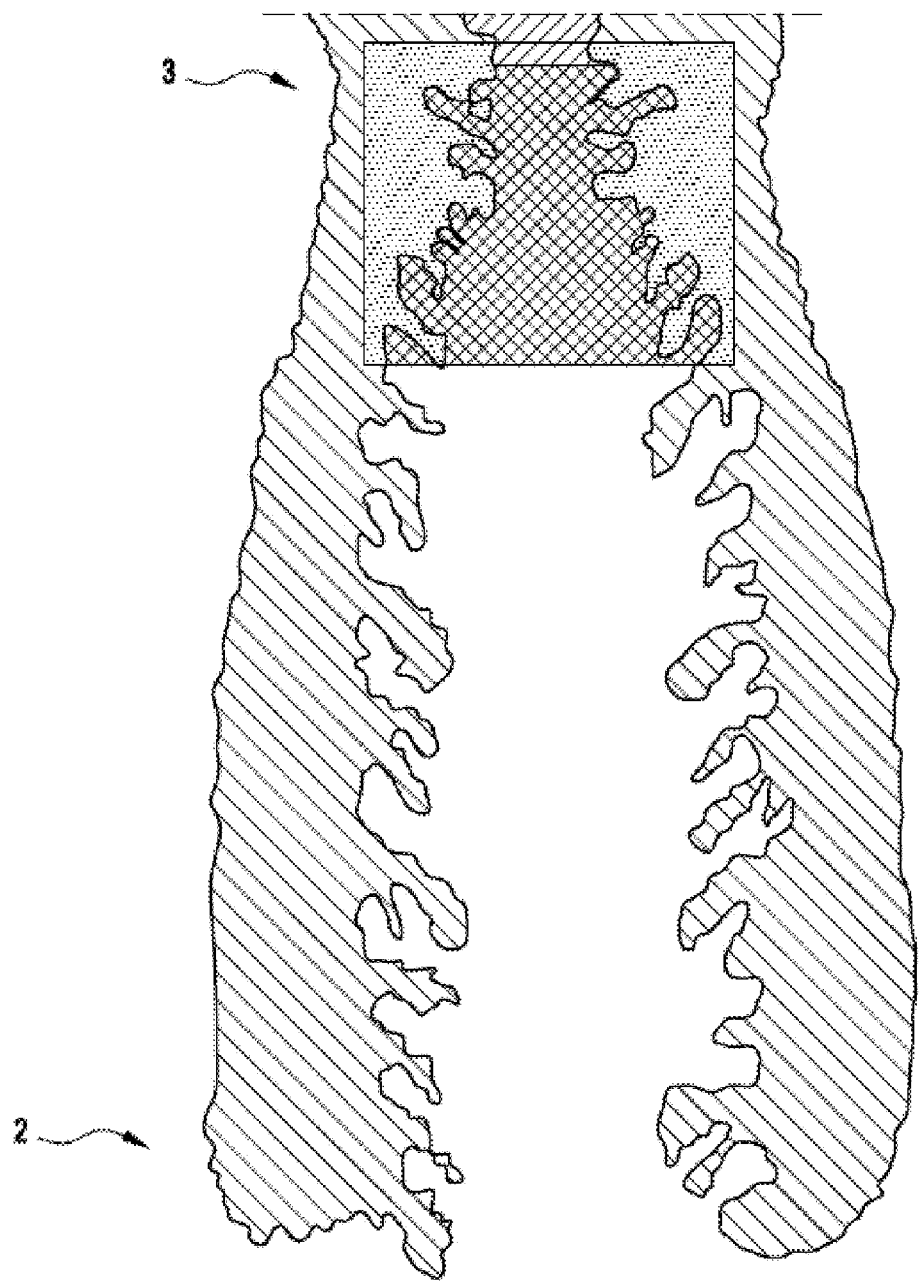
FIG. 1 shows a schematic rendering of the human cervix.

Described embodiments relate to an improved method and device adapted for transcervical sampling biological material. Embodiments are particularly suited for obtaining transcervical samples comprising fetal cells from the cervical mucus.

General Techniques and Definitions

Unless specifically defined otherwise, all technical and scientific terms used herein shall be taken to have the same meaning as commonly understood by one of ordinary skill in the art (e.g., in cell culture, fetal cell biology, molecular genetics, immunology, immunohistochemistry, protein chemistry, nucleic acid hybridization, flow cytometry, medical sampling devices and biochemistry).

Unless otherwise indicated, the recombinant protein, cell culture, and immunological techniques utilized in the present invention are standard procedures, well known to those skilled in the art.

As used herein, the term "sample" refers to a biological material. This may include biological material taken from animals, which may be mammals in some embodiments. In some embodiments, the biological material may be collected from a human being. In some embodiments, the sample may be collected from a female or a pregnant female. The female may be a human female, or may be another female mammal, which may include livestock animals such as sheep, cattle and horses, as well as companion animals such as cats and dogs. More specifically the biological material may refer to a "transcervical sample" taken directly from the cervical canal of a female comprising cervical mucus, as well as such material that has already been partially purified, or other biological material. Samples may be taken from anywhere throughout the cervical canal (internal os, external os, endocervical canal). A transcervical sample may also refer to a sample taken from the uterus (i.e intra uterine sampling including just past the internal os, endometrial sampling or CVS). Examples of such partial purification include the removal of at least some non-cellular material, removal of maternal red blood cells, and/or removal of maternal lymphocytes. In some embodiments, the cells in the sample are cultured in vitro before described methods are performed. The described embodiments of the device are not limited to taking transcervical samples, and may be used to take samples from other areas of the body, for example, the rectum, anus, or bladder from male or female humans or other species.

As used herein, the term "internal os" refers to the internal orifice of the uterus being an interior narrowing of the uterine cavity corresponding to a slight constriction known as the isthmus that can be observed on the surface of the uterus about midway between the apex and the base. The internal os is to be distinguished from the external os, which represents an aperture on the rounded extremity of the vaginal portion of the cervix, through which the cervical canal communicates with the vaginal canal.

As used herein, the terms "extracellular nucleic acids" and "cell free nucleic acids" are used interchangeably and refer to nucleic acids in the sample, which are not present within a cell and/or nuclei. Such nucleic acids are usually the result of cell death/lysis in vivo. The fetal nucleic acids can be DNA or RNA or generally a combination thereof. Preferably, the fetal nucleic acids at least comprise DNA. The free nucleic acids may be derived from, for example, the nucleous or the mitochondria.

Sampling Device

Embodiments of a sampling device and methods of use of such embodiments will now be described in further detail, with reference to the particular embodiments as detailed in FIGS. 1 through to 11.

FIG. 1 provides a schematic rendering of the front portion of the human cervix, with the entry to the cervix occurring at external os region 2 and the neck of the cervix drawing in to internal os region 3 within the body of the cervix.

Described embodiments are concerned with the recognition of internal os region 3 of the cervix as providing an optimal site for collection of biological material, which represents a valuable diagnostic and analytical tool.

Figure 2:
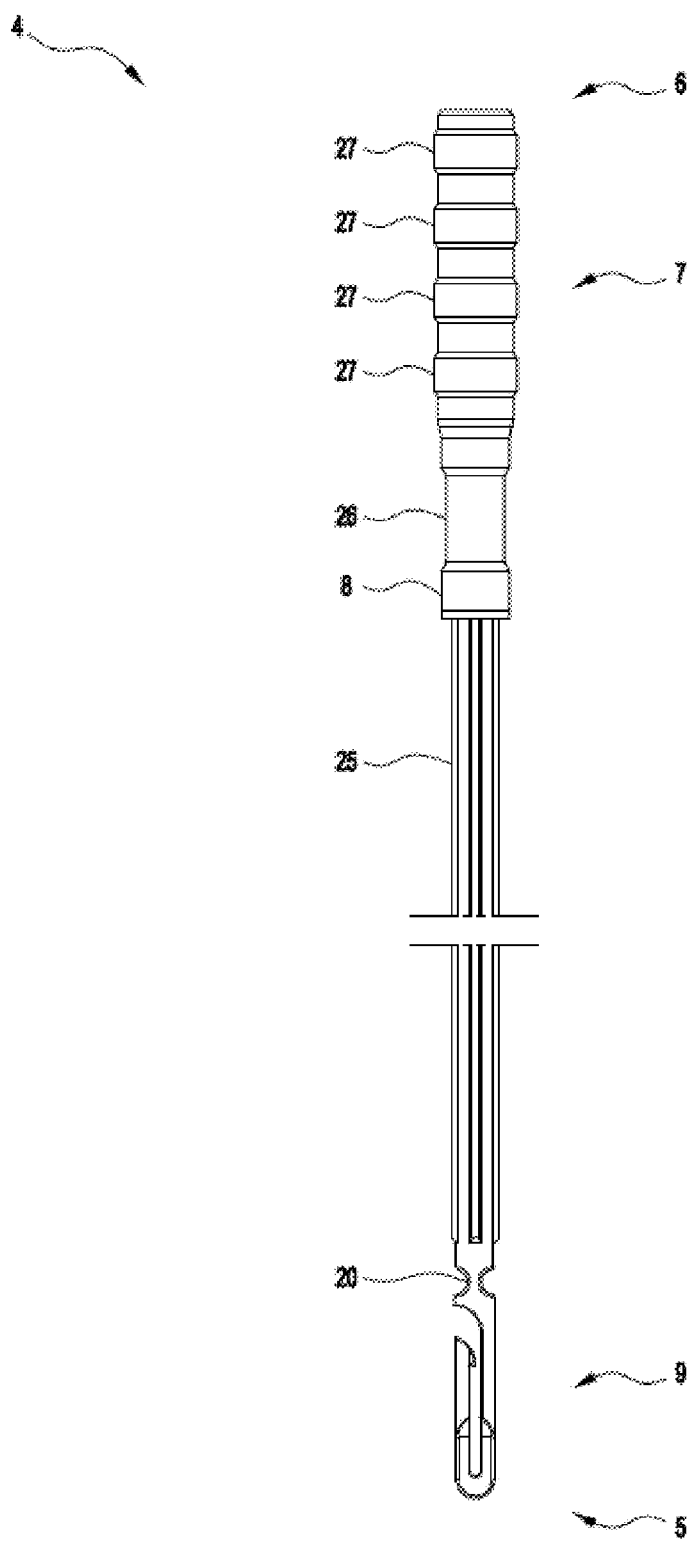
FIG. 2 shows a lengthwise view of the insertion member of the sampling device according to some embodiments.

Embodiments relate to a sampling device 1 developed for the specific purpose of allowing the user a high degree of control over the sampling methodologies and techniques with a particular emphasis on allowing the clinical user of the device to access a biological sample from internal os region 3 of the cervix. In its simplest form, sampling device 1 is represented in FIG. 2 and comprises an elongate insertion member 4 which can take the form of a hollow cylindrical tube, a substantially filled or solid cylindrical tube or rod, or any other form of elongate member or vehicle sized to allow access to the interior of the cervix. Preferably, the material used to form elongate insertion member 4 is strong and flexible enough to not snap during use, is not readily laterally compressible, is easy to mould into shape, and is biocompatible. In some embodiments, the material may be a resin, such as a transparent polypropylene random copolymer. In some embodiments, the resin used may be Bormed PP RF830MO.

Elongate insertion member 4 has at a first end 5, a sampling head 9 which is adapted for insertion into and through external os region 2 of the patient's cervix and a second end 6 having gripping portion 7 allowing the user to manipulate and operate the device by careful insertion into the cervix. Gripping portion 7 may be circumferentially enlarged compared to the elongate body (shaft 25) of insertion member 4, and may be provided with grippable texture on the surface, such as knurls, grooves or bumps, or other friction enhancing formations to provide better grip to the clinical user. In the illustrated embodiment, gripping portion 7 has friction enhancing formations in the form of a series of ridges 27.

An elongate shaft portion 25 extends between first end 5 and second end 6. Elongate shaft portion 25 is of a length to allow sampling head 9 to be inserted to an area around the internal os region 3 of the patient, while allowing a clinical user to manually manipulate sampling device 1 from outside the body of the patient. Elongate shaft portion 25 is flexible enough to conform to the internal contours of the patient but rigid enough to be easily inserted through the openings of the vagina and cervix without requiring further support.

In some embodiments, elongate shaft portion 25 may be formed with a substantially circular cross-section, while in other embodiments the cross-section may be of an oval or other non-circular shape. In some embodiments, the shape of the cross-section of elongate shaft portion 25 may be designed to restrict the degree to which insertion member 4 may be twisted when insertion member 4 is used with an outer sleeve, such as outer sleeve 10, described below.

Figure 3:
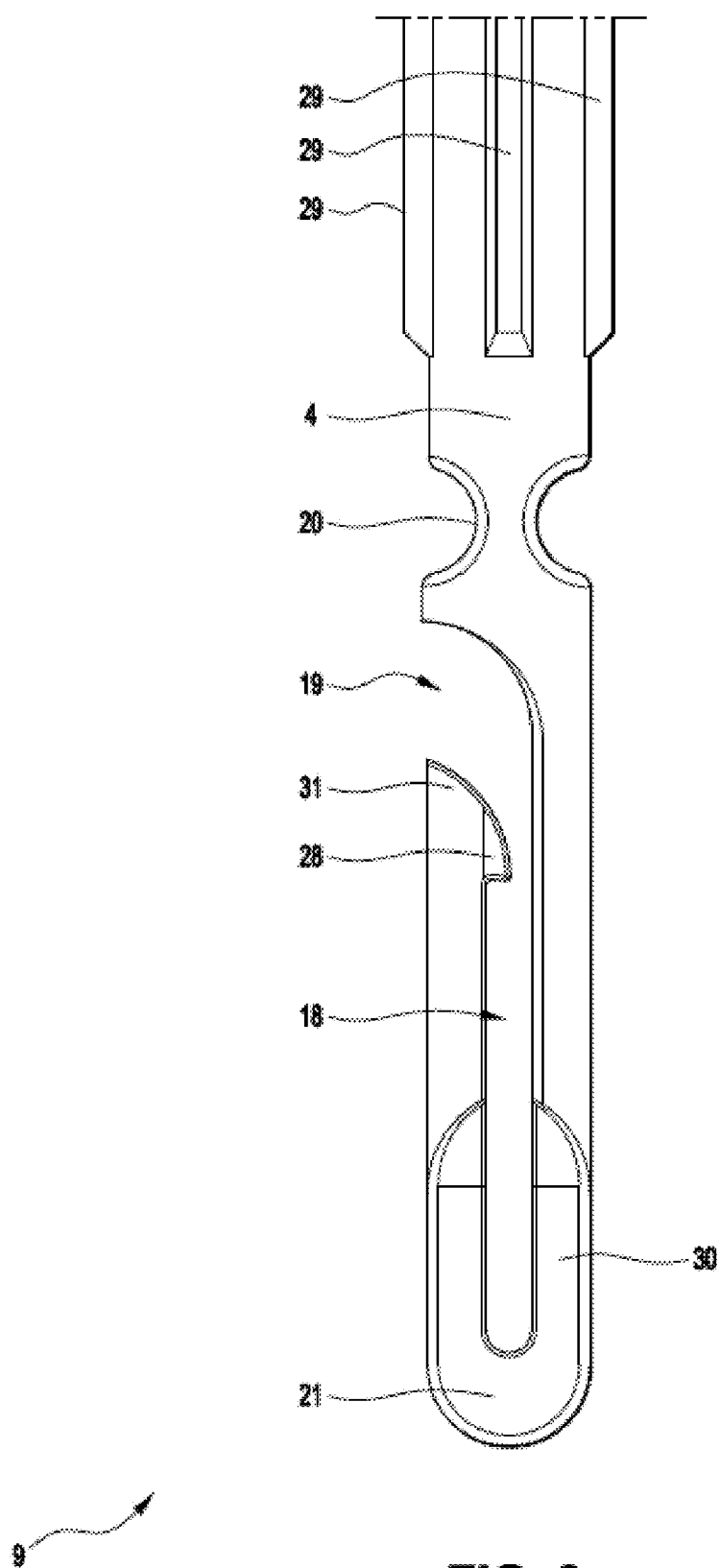
FIG. 3 shows a close-up of the sampling head of the insertion member of FIG. 2.

As best seen in FIG. 3, insertion member 4 includes a sampling head 9 having a sampling portion and a coupling portion. In some embodiments, coupling portion may comprise a terminal hook 30 forming a slot 18 with an opening 19, and the sampling portion may comprise a sampling material 14, described in further detail below. The sampling portion is coupled to the coupling portion. In the illustrated embodiment, sampling material 14 can be inserted through opening 19 of hook 30. In alternative embodiments, other forms of coupling the sampling portion to the coupling portion may be employed.

In some embodiments, slot 18 is formed to be as wide as possible to accommodate a maximum amount of sampling material 14, without necessitating a reduction in the wall thickness of hook 30 and so weakening the strength of hook 30. In some embodiments, slot 18 may have a width in the order of 0.9 mm, for example. Hook 30 preferably has a reduced thickness at its bend 21, to limit the total thickness of hook 30 and sampling material 14 when sampling material 14 is inserted through opening 19, into slot 18 and folded around bend 21 of the hook 30. Hook 30 may be designed to allow for sampling material 14 to be easily inserted during assembly, but retained in such a way that it is not readily dislodged once in position. Furthermore, the shape of hook 30 may be one that can easily be manufactured through automated machine loading.

In some embodiments, the reduction in thickness of hook 30 at its bend 21 may be in the order of 1.3 mm compared to the thickness of the straight portions of hook 30, for example. Hook end 31 may be of a smooth and rounded or slightly pointed shape to allow sampling material 14 to more easily be inserted through opening 19. Hook end 31 may further include a protrusion 28, for example shaped as a barb, to provide a partial barrier to opening 19 to help keep sampling material 14 within slot 18 and prevent or at least hinder sampling material 14 from being dislodged during use.

Insertion member 4 preferably comprises a structurally weakened portion 20 between sampling head 9 and shaft portion 25, to facilitate the separation of sampling head 9 from shaft portion 25 so that sampling head 9 can be stored, transported and processed after sampling has taken place. By providing a structurally weakened portion 20 in insertion member 4, any sampling material 14 attached to sampling head 9 does not need to be handled or removed from sampling head 9 after sampling has occurred. Sampling material 14 and sampling head 9 can then be removed as a single unit for storage and transportation.

Structurally weakened portion 20 may be a point of structural weakness such that force applied to first end 5 in a direction away from the longitudinal axis of the device would tend to cause insertion member 4 to at least bend and preferably snap or break at structurally weakened portion 20. In some embodiments, structurally weakened portion 20 may be an area of insertion member 4 that is weakened or otherwise treated or arranged to facilitate the breaking, cutting or severing of sampling head 9 from shaft portion 25 with or without the use of a separate breaking, cutting or severing implement. In some embodiments, structurally weakened portion 20 may be an area of insertion member 4 that is narrower than shaft portion 25, or it may be weakened by cut-out portions, perforations, or slits. Structurally weakened portion 20 may be marked to allow a user to visually identify its location. Structurally weakened portion 20 may be configured to be broken or snapped off manually, or may require or be aided by the use of additional tools, such as scissors, knives, clamps or files. In some embodiments, structurally weakened portion 20 may include one or more notches, recesses, defects or grooves.

In some embodiments, structurally weakened portion 20 may be configured to be separated from shaft portion 25 by a chemical, thermal or other means. For example, structurally weakened portion 20 may be formed to be dissolved or deteriorated through contact with a particular substance. In some embodiments structurally weakened portion 20 may have a lower melting point than shaft portion 25 and may be designed to be severable through the application of heat. In some embodiments structurally weakened portion 20 may be designed to be severed through a combination of means, such as through heating and subsequent application of force.

In some embodiments, sampling head 9 may be removably coupled to insertion member 4 by mechanical coupling means. In some embodiments, insertion member 4 has at one end a coupling portion. The coupling portion may be a cradle, carrier, or other receptacle to receive sampling head 9. Sampling head 9 may include a coupling portion, such as a solid base piece to be received in the receptacle, and a sampling portion, such as a plurality of fingers, tufts or sponges, or another configuration of sampling material. Sampling head 9 may be removably fastened to the receptacle by a threaded fastening mechanism such as two sets of mating threads, a 'snap' type fastener having mating lips and grooves, or a series of pawls and teeth.

Figure 4:
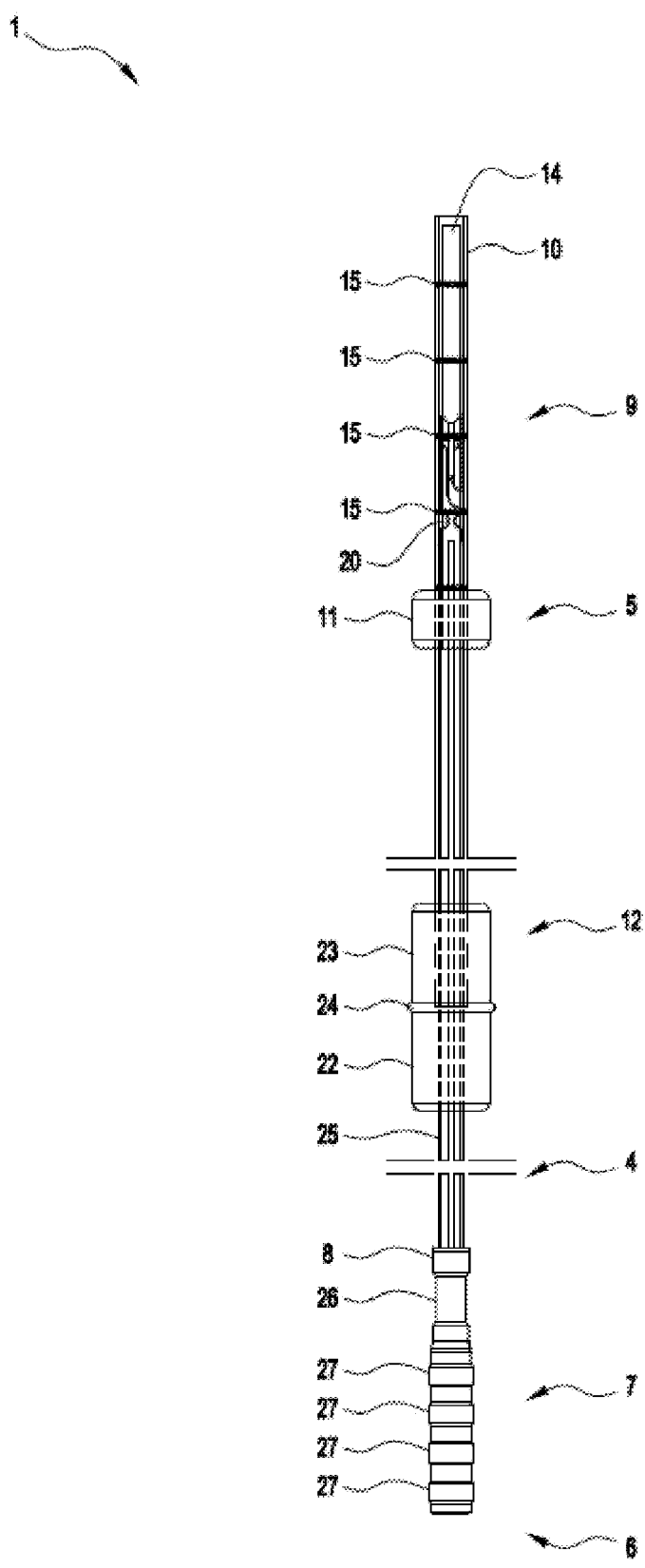
FIG. 4 shows a sampling device according to some embodiments.
Figure 5:
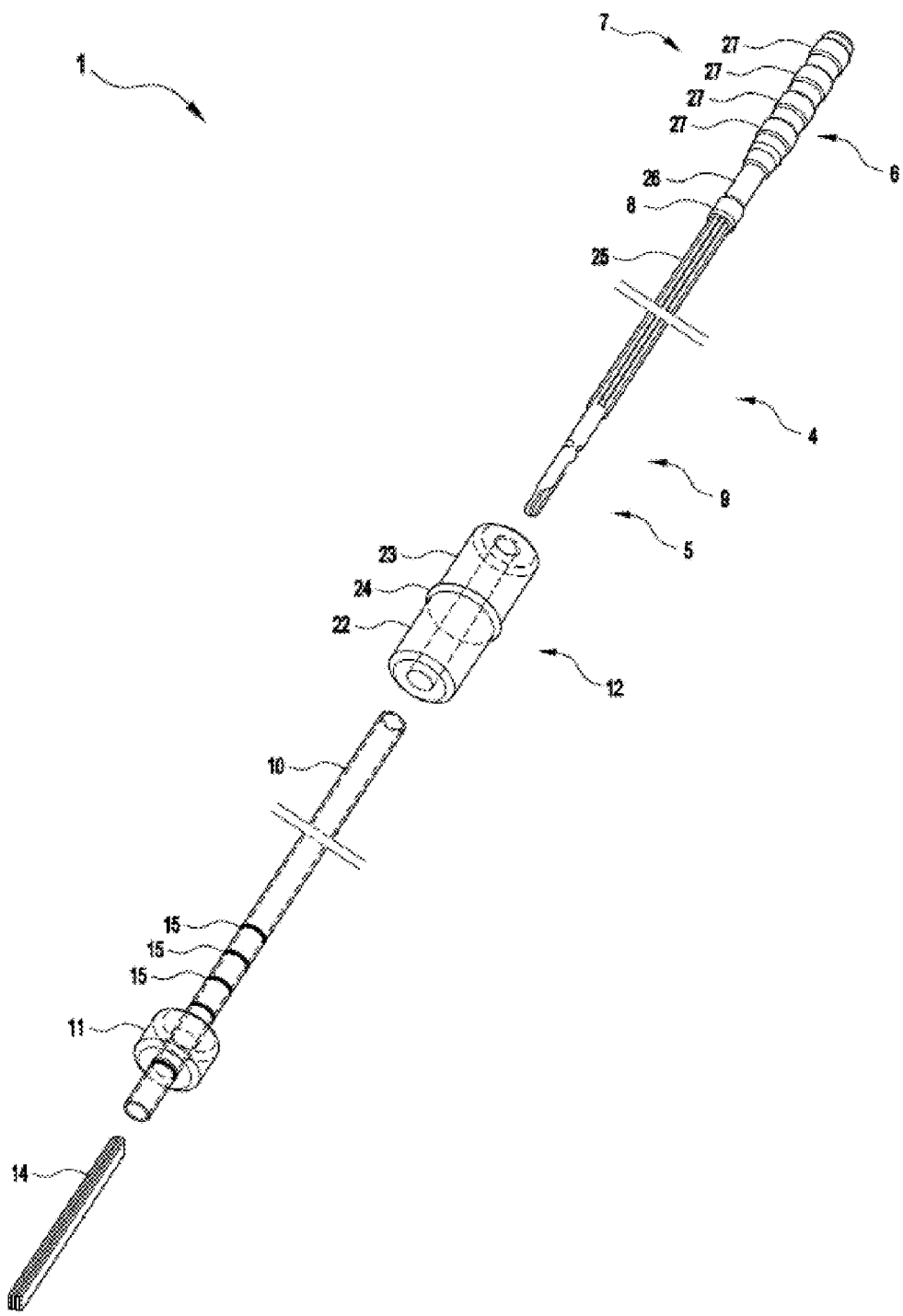
FIG. 5 shows an exploded perspective view of the sampling device of FIG. 4.

In some embodiments, insertion member 4 may be configured to be used in conjunction with additional components to improve positioning, manoeuvrability or ease of use of the device. FIG. 4 shows insertion member 4 in use with some such components, including an outer sleeve 10, to protect sampling head 9 from contamination when a sample is not being taken. FIG. 4 also shows sampling head 9 fitted with sampling material 14. FIG. 5 shows an exploded view of the components from FIG. 4.

In some embodiments, outer sleeve 10 is a hollow, cylindrical member with a substantially uniform cross section. The materials used to form outer sleeve 10 may be chosen to be strong and flexible enough so as not to snap in use, easy to mould into the desired shape, and biocompatible. In some embodiments, a translucent material may be used. In some embodiments, the material may be a low flow impact copolymer such as Moplen PP EP301G.

Outer sleeve 10 is marked by longitudinal markings 15, and is adapted for telescopic cooperation with insertion member 4, insertion member 4 being sized and configured to move within the longitudinal length of outer sleeve 10. Longitudinal markings 15 may be equidistantly spaced along a portion of outer sleeve 10, and in some embodiments may be spaced at a distance of 10 mm apart, for example. In some embodiments, longitudinal markings 15 may indicate distances of between 10 and 50 mm. Longitudinal markings 15 may be printed onto outer sleeve 10 using a medical grade ink, which may be black in colour in some embodiments. The printing may be Tampo printing, in order to withstand significant abrasion. For example, in some embodiments the printing may be robust enough to withstand a rub test such as D6279-03.2007.

In some embodiments, elongate shaft portion 25 has a series of longitudinal ridges 29 extending along its surface. In some embodiments, there may be four ridges. The ridges may be formed for the purpose of reducing the surface area of insertion member 4 that contacts outer sleeve 10, in order to assist in the tuning of the degree of frictional engagement between the inner surface of outer sleeve 10 and the outer surface of insertion member 4.

Figures 10A, 10B, 10C:
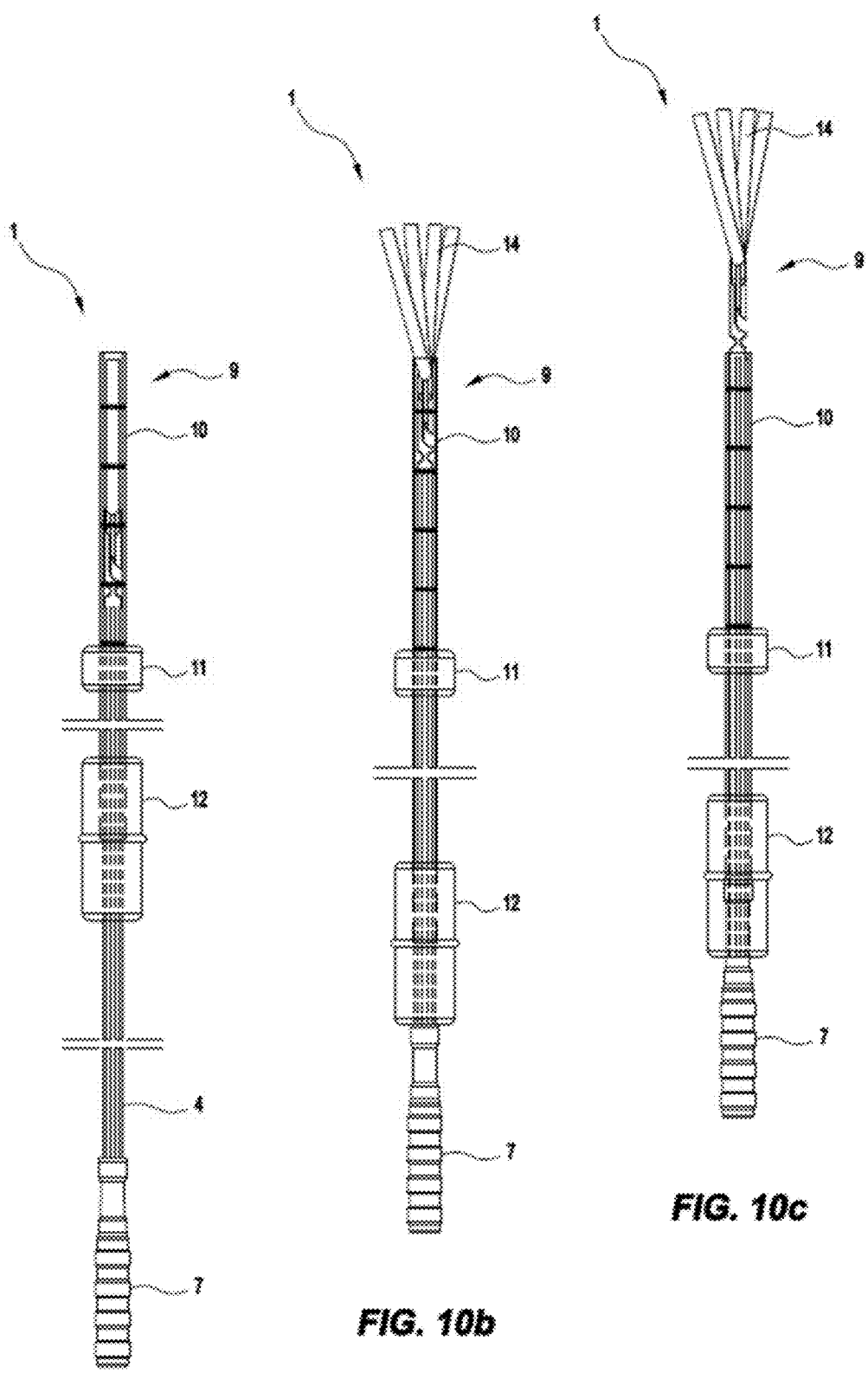
FIG. 10A shows a lengthwise view of the sampling device of FIG. 4 in a first position.
FIG. 10B shows a lengthwise view of the sampling device of FIG. 4 in a second position.
FIG. 10C shows a lengthwise view of the sampling device of FIG. 4 in a third position.

By moving through the central lumen of outer sleeve 10, insertion member 4 and sampling head 9 can be moved between three different positions relative to outer sleeve 10. Insertion member 4 and sampling head 9 can be moved to a first covered position as shown in FIG. 10A, whereby sampling head 9 is fully contained and protected within the confines of outer sleeve 10. Insertion member 4 and sampling head 9 can further be moved to a second semi-uncovered position where insertion member 4 is extended with respect to outer sleeve 10 by pushing grippable member 7 forward while holding outer sleeve 10 in place with the aid of the limiting member 12, so as to project sampling head 9 out beyond outer sleeve 10 as shown in FIG. 10B, but to keep opening 19 and structurally weakened portion 20 of sampling head 9 covered by outer sleeve 10. Insertion member 4 and sampling head 9 can also be moved to a third uncovered position in FIG. 10C, whereby insertion member 4 is extended a further amount such that opening 19 is exposed to allow for the insertion of sampling material 14 into slot 18, or for the severing of sampling head 9 from the body of insertion member 4 at structurally weakened portion 20.

The width of outer sleeve 10 is chosen to be as narrow as possible to allow for the greatest flexibility in the device, while still having an internal diameter large enough to accept insertion member 4 with sampling material 14 inserted and without sampling material 14 being under significant compression when within outer sleeve 10. The lack of significant compression reduces the risk of portions of sampling material 14 breaking off when the device is in use. In some embodiments, the width of outer sleeve 10 may be selected to accommodate sampling material 14 in its expanded state, to allow outer sleeve 10 to be returned to its first position whereby sampling material 14 is covered by and shielded within outer sleeve 10. Outer sleeve 10 and/or insertion member 4 may be formed with a bend or kink along their long dimensions to be better adapted for easy insertion into the cervix.

To assist in positioning insertion member 4 at the desired sampling location, sampling device 1 may be further provided with a positioning member 11.

Figure 6:
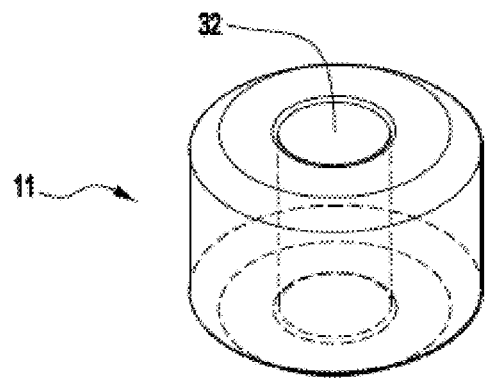
FIG. 6 shows a positioning member of the sampling device of FIG. 4.

Positioning member 11, as shown in detail in FIG. 6, may be of a generally cylindrical shape, with an inner cylindrical surface 32 defining a central lumen. Positioning member 11 is adapted to cooperate with outer sleeve 10 by movement up and down the length of outer sleeve 10 in accordance with longitudinal markings 15, which allow the insertion of the device to be specifically limited to a maximum depth as positioning member 11 gently abuts external os region 2 of the patient's cervix. In addition, positioning member 11 can also be configured to allow more comfortable and precise mating to external os region 2 by providing for partial insertion within external os region 2 and partial abutment thereto, rather than just a simple abutment to external os region 2. This may be by rounding and narrowing a distally facing side of positioning member 11 to better conform to the contour of the area around and inside external os region 2.

Positioning member 11 can be formed as a collar and can be made of rubber, plastic or other suitable materials, with the inner surface 32 being sized to have an interference fit with outer sleeve 10, such that positioning member 11 can be readily moved up and down to the appropriate depth in accordance with the physiology of the patient. The material used to form positioning member 11 may be selected to be somewhat soft to the touch to provide comfort to the patient, and to be biocompatible. It may further be chosen to be compliant enough to achieve the interference fit requirements and be flexible enough to allow movement by manual adjustment over outer sleeve 10, while reducing the risk of unintentional slippage between these components. In some embodiments, the shore hardness of the material used may be in the order of shore A 44 (ASTM D2240). In some embodiments, the material used to create positioning member may be a silicone rubber, such as Silicone Dow Q7-4840.

In some embodiments, sampling device 1 further includes a means of limiting or controlling the telescopic movement between insertion member 4 and outer sleeve 10. The means of limiting or controlling may be a set of mating components disposed on or integrated with insertion member 4 and/or outer sleeve 10. In some embodiments, these components may abut each other when a desired position of insertion member 4 relative to outer sleeve 10 is reached. Additionally or alternatively, insertion member 4 and/or outer sleeve 10 may include friction creating features that provide tactile feedback to the clinical user as to the position of insertion member 4 with respect to outer sleeve 10.

In the illustrated embodiment, the telescopic movement limiting and control is achieved through cooperation between a circumferentially expanded shoulder portion 8 of gripping portion 7, and limiting member 12. In particular, the limiting and control is achieved as shoulder portion 8 is sized to be inserted into and have an interference fit with limiting member 12.

Shoulder portion 8 at second end 6 of insertion member 4 is circumferentially larger than shaft portion 25, and may be an integrated portion of gripping portion 7. In some embodiments, shoulder portion 8 is a circumferentially enlarged portion of gripping portion 7. Shoulder portion 8 is sized to abut and, with the application of force to overcome the palpably increased frictional engagement (due to the deformation of the inner surface 33 defining a lumen of the limiting member 12), be received within limiting member 12 when limiting member 12 is moved by the retraction of outer sleeve 10. In some embodiments, the inner diameter of limiting member 12 may be in the order of 3.5 mm, while the outer diameter of shoulder portion 8 may be in the order of 4.5 mm. These measurements may be varied in order to provide an appropriate amount of frictional resistance between these components.

In some embodiments, shoulder portion 8 is smaller in length that limiting member 12, and is adjacent recessed area 26. This configuration has the effect of limiting the surface area of limiting member 12 in contact with shoulder portion 8 when shoulder portion 8 is inserted into limiting member 12. This reduces the extent of frictional engagement between these two components and reduces the amount of force needed to move them with respect to one another.

Limiting member 12 may be of a generally cylindrical shape, with inner surface 33 defining a central lumen. Limiting member 12 may be attached to outer sleeve 10 by frictional engagement and adapted for movement up and down the length of the insertion member 4 together with outer sleeve 10. Limiting member 12 may be made of rubber, plastic or other suitable materials. The material and size of limiting member 12 may be selected to give an interference fit between limiting member 12 and outer sleeve 10, keeping limiting member 12 frictionally engaged with outer sleeve 10. The material may be chosen to be compliant and flexible enough to give the interference fit required and allow movement of limiting member 12 with respect to outer sleeve 10, while reducing the risk of unintentional slippage between these components. In some embodiments, the shore hardness of the material used may be in the order of shore A 44 (ASTM D2240). The material used to create limiting member 12 may further be chosen to be somewhat soft to the touch, for the comfort of the patient, and to be biocompatible. In some embodiments, the material may be a silicone rubber, such as Silicone Dow Q7-4840.

Figure 7:
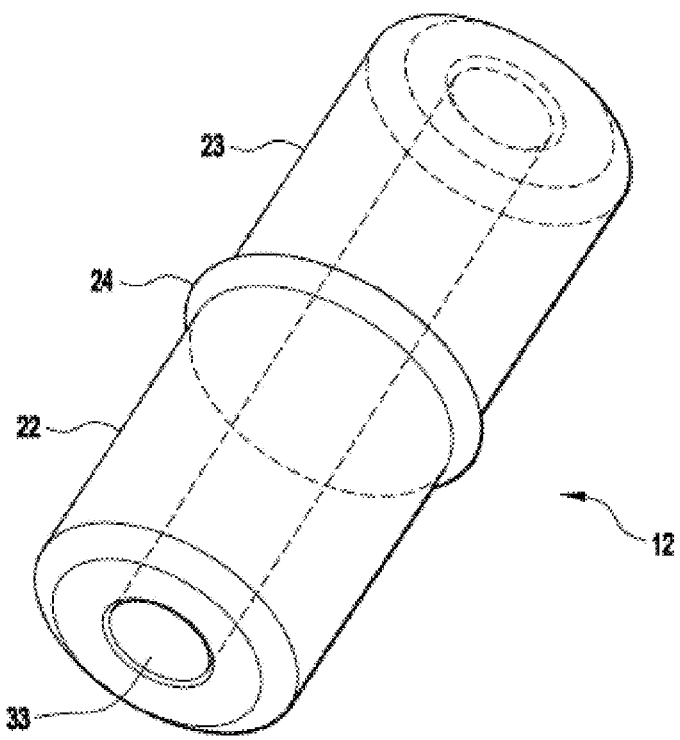
FIG. 7 shows a limiting member of the sampling device of FIG. 4.
Figure 8:
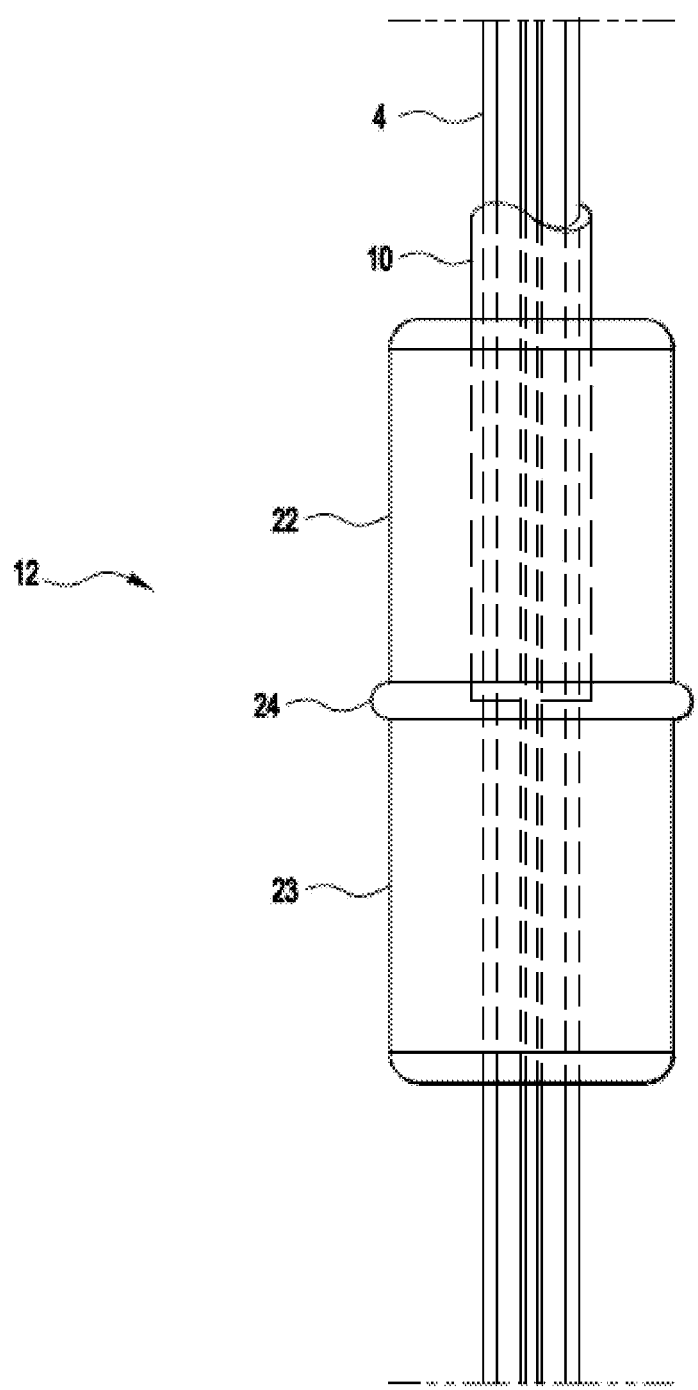
FIG. 8 shows a close-up view of the limiting member as positioned on an outer tube of the sampling device of FIG. 4.

Limiting member 12, as shown in detail in FIG. 7, may be formed as two tubular sections 22 and 23, with a ridge 24 formed in between. Ridge 24 can form a visual guide for the assembly of limiting means 12 onto outer sleeve 10, indicating the depth of insertion of outer sleeve 10 into limiting member 12, as seen in FIG. 8. For this purpose, limiting member 12 may be substantially transparent or translucent. Ridge 24 may also form a flange on the inside of limiting member 12 to provide a tactile means of indicating the depth of insertion of outer sleeve 10 into limiting member 12.

The use of the positioning member 11 and limiting member 12 allows a variety of uses of the device. For example, the device may be configured such that sampling head 9 can be stopped at a precise position within the patient's cervix, such as at internal os region 3. This may be done by the introduction of outer sleeve 10 into the cervix at a point forward of internal os region 3 in accordance with the positioning member 11. Limiting member 12 could be positioned on insertion member 4 such that once the device is inserted into the cervix, outer sleeve 10 can be retracted to the second position. This would uncover sampling material 14, which in embodiments used for transcervical sampling, would be positioned at a position close to or immediately adjacent the internal os region 3. In the second position, limiting member 12 contacts and abuts shoulder portion 8, hindering the outer sleeve 10 from further retraction, which might uncover hook 30, and which may make sampling material 14 susceptible to dislodgement.

In another use, instead of retracting the outer sleeve, the insertion member 4 may instead be extended, with positioning member remaining in contact with external os 2. In this case, sampling material 14 may extend past internal os 3, or it may be restricted from passing by a naturally occurring mucus plug (if present), depending on the viscosity of the mucus plug and the properties of the sampling material.

In another use, the device may be configured such that sampling head 9 can be stopped at a pre-determined position within the patient's cervix, such as a distance lower than internal os 3, such that when insertion member 4 is moved within the outer sleeve 10 to the second extended position, it would progress the insertion of sampling head 9 up to the pre-determined position of internal os region 3, whereby limiting member 12 contacts and abuts shoulder portion 8, limiting the movement of sampling head 9 past the desired position within the patient's cervix.

After sampling, limiting member 12 can facilitate in the movement of the device to the third position, to allow for the uncovering of the structurally weakened region 20 by the outer sleeve 10 and easy removal of sampling head 9. By applying enough force to limiting member 12 to overcome the frictional engagement and abutment between limiting member 12 and shoulder portion 8, outer sleeve 10 can be further retracted with respect to insertion member 4, allowing opening 19 of sampling head 9 to become exposed.

The positioning of positioning member 11 can be set by the patient's practitioner using knowledge of the cervical length gained from ultrasound or other techniques. For example, an alternative technique may be the use of tables charting the average cervix length of women at particular periods of their pregnancy. In one embodiment, the tip of insertion member 4 and/or outer sleeve 10 may be coated or impregnated with a material clearly visible using ultrasound. Such a material could include silver, with antibacterial properties. Alternatively, air bubbles could be formed in the tip of sampling head 9. In this manner, the device could be readily calibrated for each patient thereby ensuring optimal precision and insertion for sample collection at internal os region 3 of each particular patient. The use of an ultrasound marker may be particularly useful where no cervical measurement is available, or as an additional safety feature.

The sampling head 9 is most preferably formed of or includes a compliant and absorbent sampling material 14 which is capable of being formed into an open cell foam or sponge configuration providing a level of compliance in the virgin state so as to ensure that the insertion of sampling device 1 into the cervix does not abrade, tear or in any way damage the lining of the cervix prior to absorption of the sample from internal os region 3, whereby sampling material 14 will expand and soften due to the absorption of biological fluids associated with the cell sampling.

Sampling material 14 may be selected from polyvinyl acetate, polyvinyl acetal, polyurethane, cellulose or any other suitable absorbent material and is preferably provided in a manner such that small pieces or fibres of sampling material 14 will not shed at any stage during the sampling procedures. The open cell sampling material 14 of the porous head is substantially porous having preferably about 90% of open cells and most preferably including 100% open cells. Sampling material 14 is preferably hydrophilic with materials most preferably chosen that are hydrophilic in an untreated state. Alternatively, sampling material 14 may be treated so as to alter the surface energy or polarity including plasma or chemical treatment methods.

Sampling material 14 is preferably configured to provide maximum capture of mucal biological material by adsorption onto the surface of sampling material 14, by maximizing the surface area of sampling material 14. A configuration of sampling material 14 as a multifilamentous array of sponge or sponge-like fingers as detailed in FIG. 9 forms one embodiment. In some embodiments, sampling material 14 may be formed from an 8" length of eye wick material folded in half twice and then trimmed to form four fingers of sampling material. In another embodiment, sampling material 14 may be formed from a 4" length of eye wick material folded in half once to form two fingers of sampling material. This may be particularly used in an embodiment where outer sleeve 10 is moved back to cover sampling head 9 before sampling device 1 is withdrawn, as a smaller quantity of sampling material 14 will allow sampling material 14 to fit back within outer sleeve 10 even in its expanded state. In another embodiment, sampling material 14 may be formed of 6, 8, 10, or another suitable number of fingers of sampling material. In some embodiments, where sampling material 14 is not folded in half, sampling material 14 may additionally be formed of 1, 3, 5, 7, 9, or another suitable number of fingers of sampling material.

The pore size of sampling material 14 is preferably sized between 10 to 2000 microns with an average pore opening over the whole of sampling material 14 of between 400 to 1000 microns. The distribution of pore size throughout sampling material 14 could be consistent or random in accordance with the particular requirements to which sampling device 1 may be applied. The outer surface of sampling material 14 is preferably configured such that the outer pores of sampling material 14 are no smaller than the pore size throughout sampling material 14 of sampling head 9 so as to ensure that the outer or surface pores of sampling material 14 are not closed off or permanently filled or coated upon access to the sampling site in a manner that may reduce the ability of sampling head 9 to rapidly and efficiently absorb the sample.

The pore size and distribution may enable a large variety of material to be collected. For example, in some embodiments, sampling material 14 may be able to collect matter sized from the molecular to the cell level. This may give the device possible uses in diagnostic applications such as the detection of cancers (including vaginal, cervical, uterine, endometrial, ovarian), viruses (such as the human papillomavirus (HPV) human cytomegalovirus (HCMV) and herpes simplex virus type 2 (HSV) type 1 and type-2) and infection (for example, Chlamydia trachomatis and Neisseria gonorrhoeae), use in forensic applications for the collection of sperm in sexual assault cases, and use in prenatal diagnosis and therapy through the collection of material such as extracellular fetal nucleic acids (DNA/RNA), fetal cells, free fetal nuclei, microRNAs (miRNAs) and protein for the detection of genetic abnormalities, parentage testing, prediction of pregnancy and the prediction of many pregnancy complications, including but not limited to pre-term labor, pre-eclampsia, fetal growth restriction, fetal congenital heart defects and fetal neural tube defects by way of non-limiting example.

The absorption characteristics of sampling material 14 may be configured to provide a fixed and predetermined quantity of absorptive capacity so as to allow sampling device 1 to absorb and adsorb a known and predetermined quantity of liquid and mucus beyond which no further biological material will be absorbed. In this manner, sampling device 1 can be used in a manner ensuring that only the most relevant sample is collected from internal os region 3 and the risk or chance of contamination of sampling head 9 with further absorption of cells from other regions of the cervix as sampling head 9 is withdrawn from the patient are minimized.

In addition, the outer surface of sampling material 14 may be coated with a temporary coating to delay absorption. Such a dissolvable substance or material can be used with a time delay function such that the outer surface coating of sampling material 14 is dissolved after insertion of sampling head 9 into the cervix and with sufficient delay to allow sampling head 9 to be correctly positioned at the optimal point at internal os region 3. In this manner, the absorptive function of sampling material 14 will be protected from premature absorption during insertion through the cervix.

Figure 9:
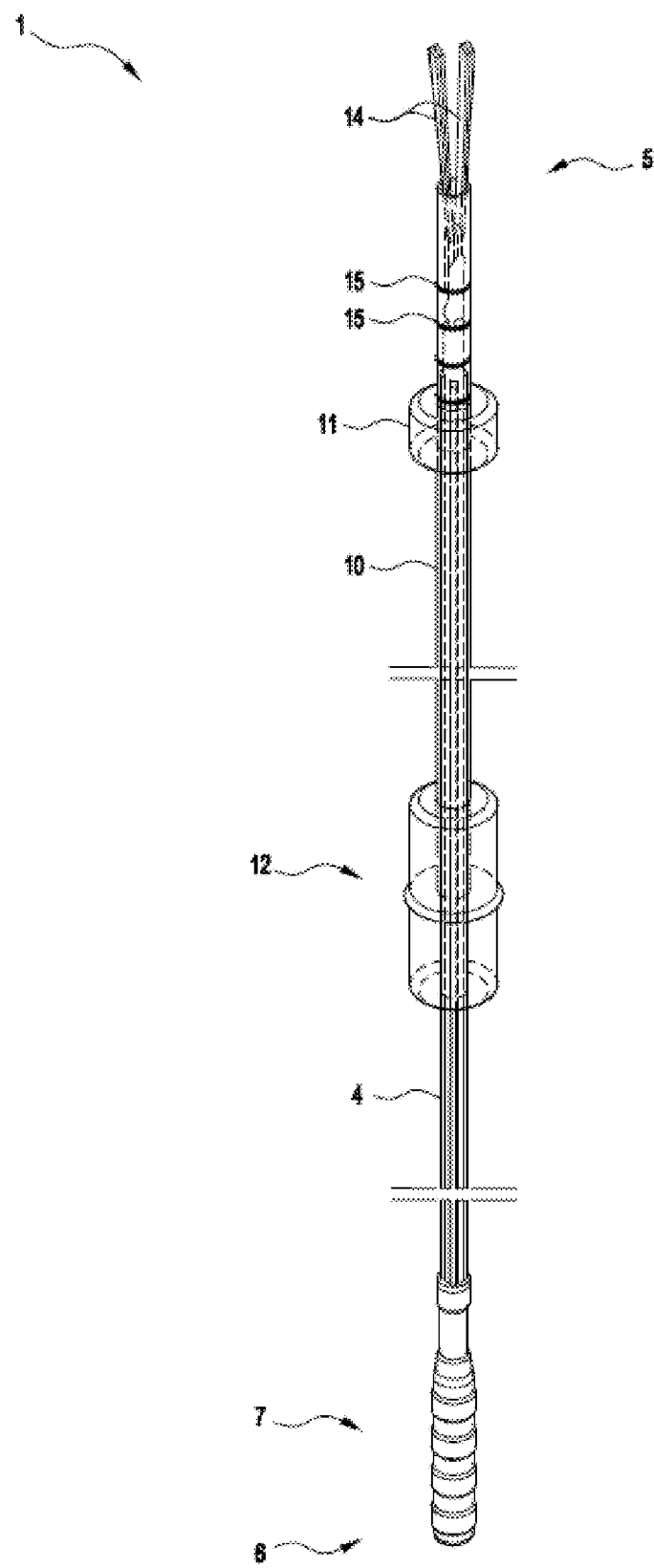
FIG. 9 shows a perspective view of the sampling device of FIG. 4 with a sampling portion exposed.

The form of sampling head 9 can be configured to adopt a wide range of shapes. The surface collection of the sponge also allows for the collection of clumps or aggregations of samples or other biological material larger than the actual pore size particularly mucus which is adsorbed onto the surface. Sampling head 9 may have multiple pieces of foam or sponge as strips as sampling material 14 as shown in FIG. 9. The most preferred biological material as a source of fetal cells is mucus which has been found to collect most effectively by adsorption onto the surface of sampling head 9 and absorption into the interior of sampling material 14. In this manner the highest surface area to volume ratio as provided by a multifilamentous array of sponge or sponge-like fingers as shown by sampling material 14 in FIG. 9 provides one embodiment for effectively sampling biological material.

The configuration of sampling head 9 is preferably designed to maximize absorption from the optimal region of internal os region 3 and may have a prior absorptive length of between 0.5 and 5 cm with an expanded volume of between 0.01 and 3 cubic cm, for example. The preferred predetermined quantity of said cells or sample can be set between 0.01 ml and 3 ml in accordance with the physiology of the patient.

The individual components of sampling device 1 such as insertion member 4, positioning member 11 and limiting member 12 may be injection moulded or formed by any other suitable means. The materials used in all the components of sampling device 1 should be able to be sterilized by radiation or some other like method as may be commonly used in the medical device manufacture industry.

Some embodiments relate to a method of sampling biological material from a patient which will be described in more detail with reference to FIGS. 10 and 12 to 14.

The methods of some embodiments comprise the steps of introducing sampling device 1 into the cervix of a patient whereby sampling device 1 includes sampling head 9 positioned at internal os region 3 of the patient's cervix whereby the sample is taken from internal os region 3 of the patient and sampling device 1 subsequently withdrawn from the patient and the collected biological material is then harvested.

In some embodiments, the steps include the pre-measurement of the cervical canal length of the patient by ultrasound or other means, whereby adjustable stop means of sampling device 1, as previously described, can be set so as to position sampling head 9 at or near internal os region 3 of the patient's cervix. Once the measurements and settings are complete, the device can be inserted into the patient with positioning member 11 gently abutting external os region 2 such that sampling head 9 is correctly positioned at internal os region 3 whereby sampling head 9 can be left to absorb the cell sample and most preferably absorb the predetermined quantity of cell sample materials whereby the device can then be removed and the biological material harvested and collected. This can be achieved by first severing the device at structurally weakened portion 20, and removing sampling material 14 along with hook 30, and then processing the material collected by sampling material 14 in an appropriate way.

Referring to FIG. 10, the sampling methods according to some embodiments utilize cell sampling device 1 as previously described. Referring now to FIG. 10A, one method includes the step of providing a preliminary measurement of the cervical length of patient by ultrasound or other suitable means, such as the use of a table of average cervix lengths during pregnancy. Once the cervical length of the patient is determined and the precise position of internal os region 3, sampling device 1 can be adjusted such that positioning member 11 is adjusted such that outer sleeve 10 is left with a projection through external os region 2 sufficient to allow sampling head 9 to be extended whereby the further reach achieved positions sampling head 9 at internal os region 3.

In another possible use of sampling device 1, positioning member 11 is adjusted using longitudinal marking 15 to a distance from the end of outer sleeve 10 corresponding to the length of the cervix measured. In this use, sampling head 9 is positioned at the level of internal os region 3 in an unextended (covered or shielded) position, in which it is disposed within the outer sleeve 10, and sampling material 14 may be moved or projected at least partially beyond internal os region 3 when insertion member 4 is extended.

Referring now to FIG. 10B the precise extension of sampling head 9 by way of telescopic movement of insertion member 4 via gripping portion 7 is provided by limiting member 12 which allows sampling head 9 to be duly extended into internal os region 3 once sampling device 1 has been inserted into the patient with positioning member 11 abutting external os region 2. In use, in this method the device would be inserted into the patient such that sampling head 9 is fully protected within the confines of outer sleeve 10 during the insertion process. In this configuration, the device would be gently inserted into the patient with the protruding portion of outer sleeve 10 penetrating external os region 2 only so far as positioning member 11 which would then abut external os region 2 so as to provide the preliminary insertion of the device, partially within the cervix of the patient. Once this is achieved, the operator could then gently extend sampling head 9 by moving gripping portion 7 so as to telescopically extend insertion member 4, relative to outer sleeve 10 so far as limiting member 12 would allow as per FIG. 10B. At that point, sampling head 9 would have been moved out of the confines of outer sleeve 10 and caused to position itself precisely at internal os region 3, or in some embodiments, slightly past internal os region 3. The extent of insertion of sampling material 14 may be limited by a natural mucus plug (if present) at internal os 3, and factors such as the viscosity of the mucus plug and the properties of sampling material 14. Once sampling head 9 is positioned at internal os region 3, it is allowed to remain in position for a predetermined time until the predetermined quantity of sample is fully collected from internal os region 3, such that no further sample is capable of being collected.

Referring now to FIG. 10C, the third position of insertion member 4 with respect to outer sleeve 10 is shown. In this position, the entirety of sampling head 9 is exposed, along with slot 19 and structurally weakened portion 20. This position is reached when second tubular portion 23 of limiting member 12 internally receives shoulder portion 8 of insertion member 4. This requires the application of pressure to overcome the friction between limiting member 12 and shoulder portion 8, which provides the clinical user with a tactile means of knowing what position insertion member 4 and outer sleeve 10 are in, and reduces the risk that insertion member 4 and outer sleeve 10 move into the third extended position inadvertently. It also protects structurally weakened portion 20, to reduce the risk that this portion is broken or severed in use, before it is desirable for sampling head 9 to be removed.

The third position has several purposes. When sampling device 1 is being initially assembled, moving the device into the third position allows for sampling material 14 to be inserted into slot 18 of sampling head 9. After sampling, in some embodiments, the device may be returned to the third position to uncover structurally weakened portion 20, to allow for the removal of sampling head 9 from shaft portion 25. Alternatively, sampling material 14 may be removed back through opening 19.

Figure 16:
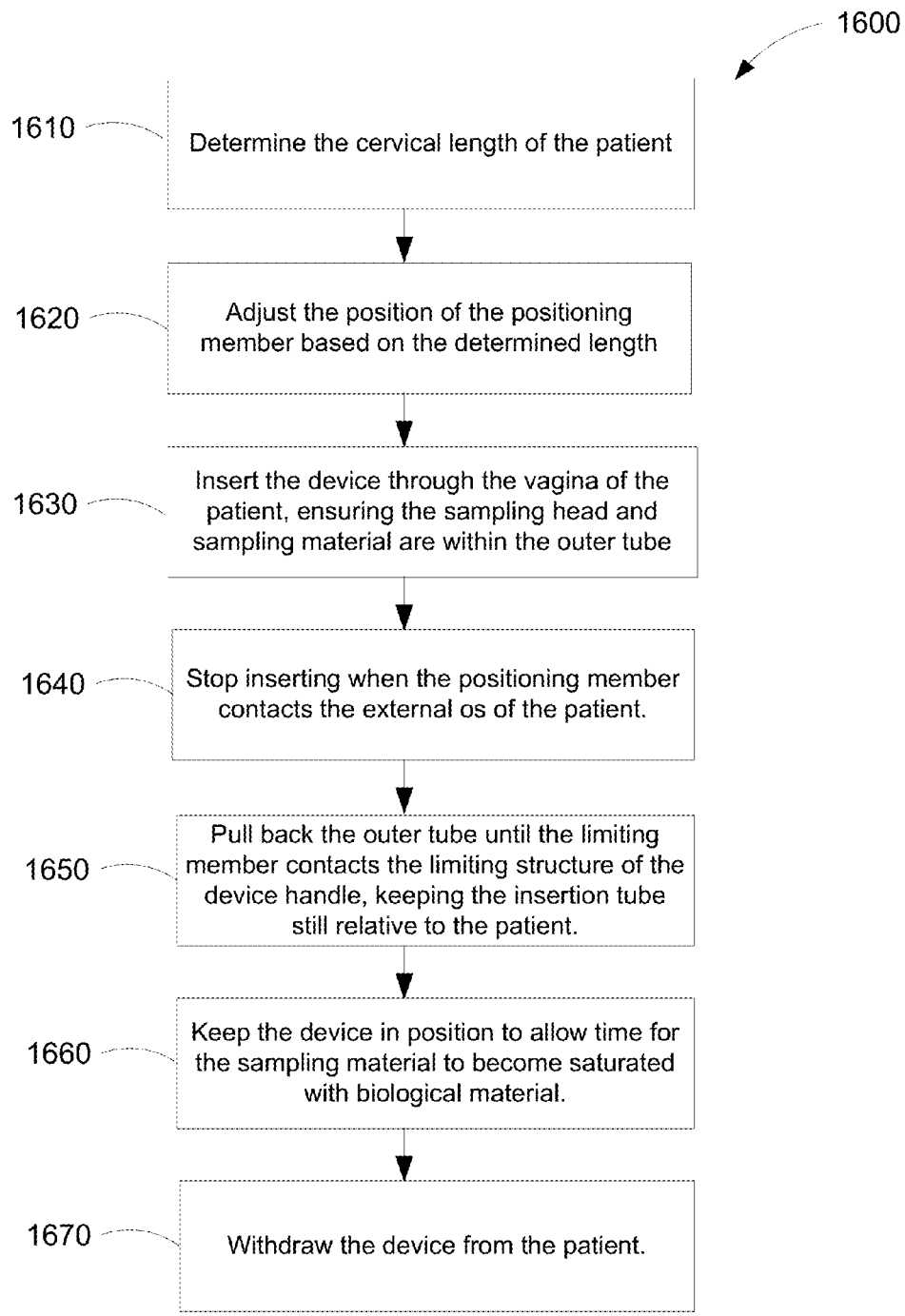
FIG. 16 is a flowchart of a method of using the device of FIG. 4 to obtain a biological sample.

The methods can alternatively utilize the device as previously described in a different sampling method as shown in FIG. 11 and the flow diagram of FIG. 16. At 1610, the cervical length of the patient is determined. This may be done by ultrasound or other means, such as with the use of tables charting the average cervix length of women at particular periods of their pregnancy. The sampling methods in this embodiment proceed at 1620 by setting positioning member 11 along the length of outer sleeve 10 at such a position that the full extent of outer sleeve 10 occurs at internal os region 3 in the patient's cervix. Limiting member 12 is positioned on insertion member 4 so as to position sampling head 9 within the confines of outer sleeve 10. Once sampling device 1 is so set, the device is carefully inserted into the patient's cervix at 1630 until positioning member 11 can be tactilely sensed to gently abut external os region 2 at 1640. At this stage, insertion member 4 is fully extended but such that sampling head 9 is still protected within the confines of outer sleeve 10. In this manner, the device allows for the full protection of sampling head 9 during entry into the cervix so as to prevent any contamination or sampling from inappropriate regions of the cervix. At this stage, sampling head 9 is ready to be exposed at 1650 with the exposure accomplished by gently and carefully withdrawing outer sleeve 10 relative to external os region 2 and positioning member 11 while ensuring that insertion member 4 and sampling head 9 remain positioned relative to internal os region 3. In this manner, outer sleeve 10 is gently withdrawn from sampling head 9 allowing sampling head 9 exposure to internal os region 3 for absorption of the cell sample. The device is then left in this position at 1660 for a specified period, being an appropriate length of time for the sampling material 14 to absorb up to a predetermined quantity of sample (based on the maximum absorptive or adsorptive capacity of the sampling material 14) and once a quantity of sample has been collected, the device can be gently removed at 1670 and the harvested biological material collected. In some embodiments, the specified period may be in the order of between 1 second and 10 minutes. In some embodiments, the device may be kept in place for a period of time in the order of 5, 10, 20, 30, 40 or 50 seconds, or 1, 2, 3, 4, 5, 6, 7, 8, or 9 minutes. In some embodiments the specified period may be another number of seconds or minutes, generally within the range indicated above.

In some embodiments, outer sleeve 10 may be pushed back into the first position to cover sampling head 9 before the device is withdrawn, to avoid contamination of the sample with material from the regions through which sampling device 1 passes as it is withdrawn. For such embodiments, at least the distal end section of outer sleeve 10 may be diametrically enlarged in proportion to a remainder of outer sleeve 10 to accommodate the engorged size of sampling material 14, as sampling material 14 may expand after sampling and so may not fit back into the same space as it would occupy before sampling. This may be done by increasing the diameter of part or all of outer sleeve 10, decreasing the size or amount of sampling material 14, or both.

In addition to the above, the device allows the previously described methods to incorporate the use of aspirating systems whereby a simple cylinder and barrel or plunger connected to a separate syringe or alternative vacuum system, can be incorporated to assist in the suction or removal of cervical mucus if such additional assistance is deemed to be required. In this aspect, outer sleeve 10 can form a suitable conduit from the vacuum to the region of sampling head 9.

In the aspirating embodiment of the device, a plunger may be used to push out sampling head 9 before it is withdrawn to aspirate the sample and a syringe could be temporarily or permanently attached to the device prior to insertion into the cervix. The syringe may connect via a luer-style fitting to a tube that either temporarily houses or is connected to sampling material 14 of sampling head 9. Alternatively, any other manual pumping device including a fixable tube or bladder could be incorporated in a similar manner. In addition to the above, a powered device could be used to provide suction necessary to aspirate the sample, the powering device could take the form of a pump, it could be used to provide continuous or intimate suction until the desired sample volume is obtained as an alternative to absorbing the sample by passive suction only. Such an option may allow for the repositioning of a device while sampling if the original positioning appears to require adjustment.

The fluid or sample could be aspirated into the tip or barrel of insertion member 4 directly or most preferably the tip of the tube could be adapted to protrude beyond the outermost portion of sampling head 9 and/or remain within or partway through sampling head 9. The aspirating barrel, which may be incorporated in a function of outer sleeve 10 and/or insertion member 4, could be configured to ensure that any fluid aspirated must pass through sampling head 9. In this manner, sampling head 9 could act as a diffuser for the suction so that whilst advice is capable of aspirating a volume of fluid and mucus, the sponge and passive action of the device as previously described, reduces the aspirating pressure required and/or experienced in any part of the cervical canal during sample collection.

Although the described embodiments generally refer to a device for the taking of a biological sample, the described device can be alternatively used to deposit or deliver a substance to a region of the body. For example, the sponge material 14 may be impregnated with a medicament or anaesthetic or other substance, and used to deliver that substance to the internal os of a female human, another part of the cervical canal or another area of a body of a subject.

Figure 14:
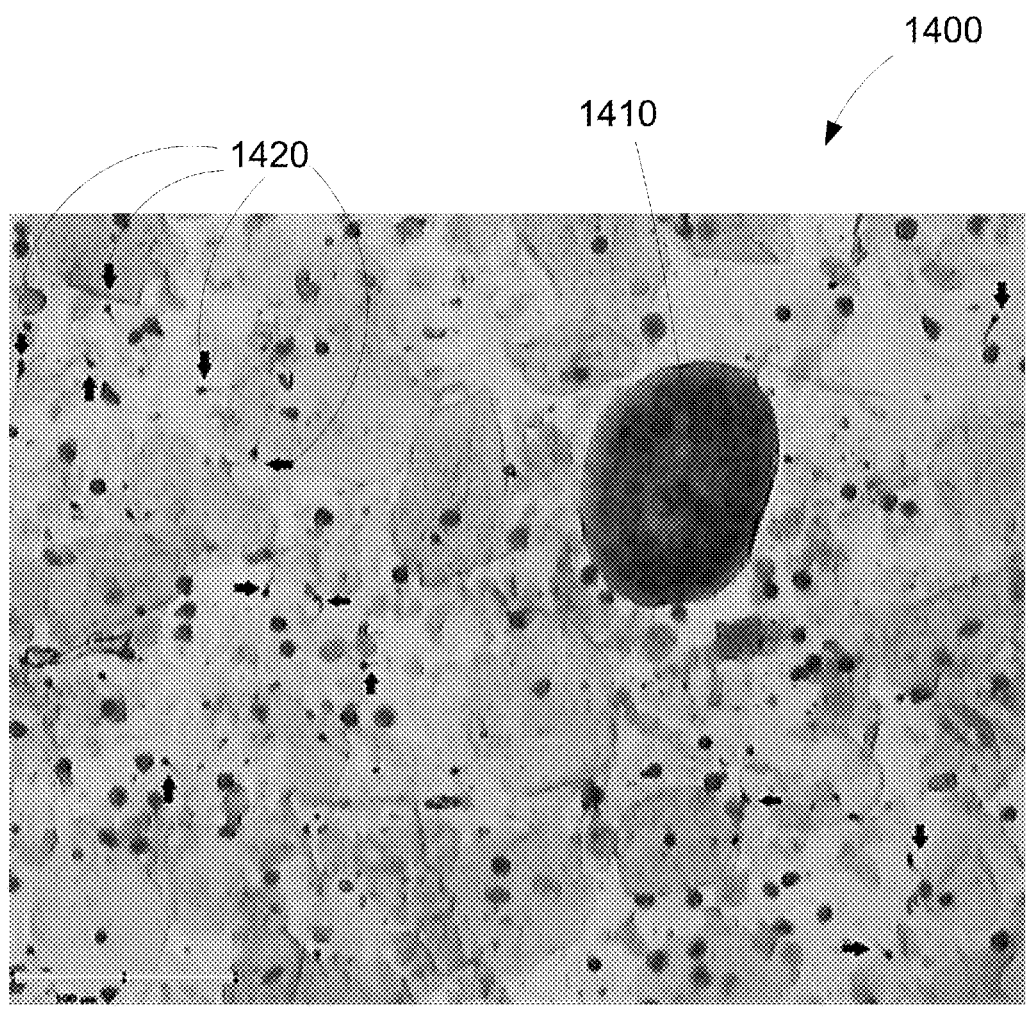
FIG. 14 is an example image of syncytiotrophoblasts and spermatozoa that can be obtained using the sampling device of FIG. 4.

FIG. 14 provides an example of a syncytiotrophoblast 1410 obtained with sampling material 14. The sample 1400 was obtained at the level of internal os region 3 of a 38 year old human female (referred to as Patient 893) who was 6 weeks pregnant and the cells stained with hematoxylin and eosin staining. Visual examination of the sample showed that the sampling material 14 also provided a good method for harvesting sperm, indicated by arrows 1420. The device includes many advantages as detailed above and also further includes the advantages whereby the slow absorption rate of the sponge-like sampling head 9 minimizes possible rupture of the cervical plug as sometimes occurs during the use of active sampling techniques. The device minimizes such possibilities and accordingly minimizes the possibility of infection and complications as a result of such ruptures. In addition, the soft physical features of sampling head 9 provides invasiveness and discomfort and allows a patient to partake in multiple sampling exercises within a short period of time without undue trauma. Furthermore, the gentle nature of sampling device 1 allows the time that sampling device 1 can be left in position to collect a sample to be extended from the expected time required of about 1 to 2 minutes up to 48 hours if this is so required. The particularly gentle nature of the device allows such use if required.

The described device and methodologies provide a highly reliable means and method of obtaining consistent and high quality biological material comprising fetal cells previously only obtainable by more invasive methods as previously described.

Assembly, Storage and Transport

In some embodiments, the components of sampling device 1 (other than sampling material 14) are injection moulded or formed by some other means known in industry, and must be assembled before use. This may require a number of steps to be performed. In some embodiments, these steps would need to be performed in a sterilized environment, and (if performed manually) the operator performing the assembly would be required to wear gloves to prevent contamination of the device. The manufacturing process, including assembly, may be partially or entirely automated.

Figure 15:
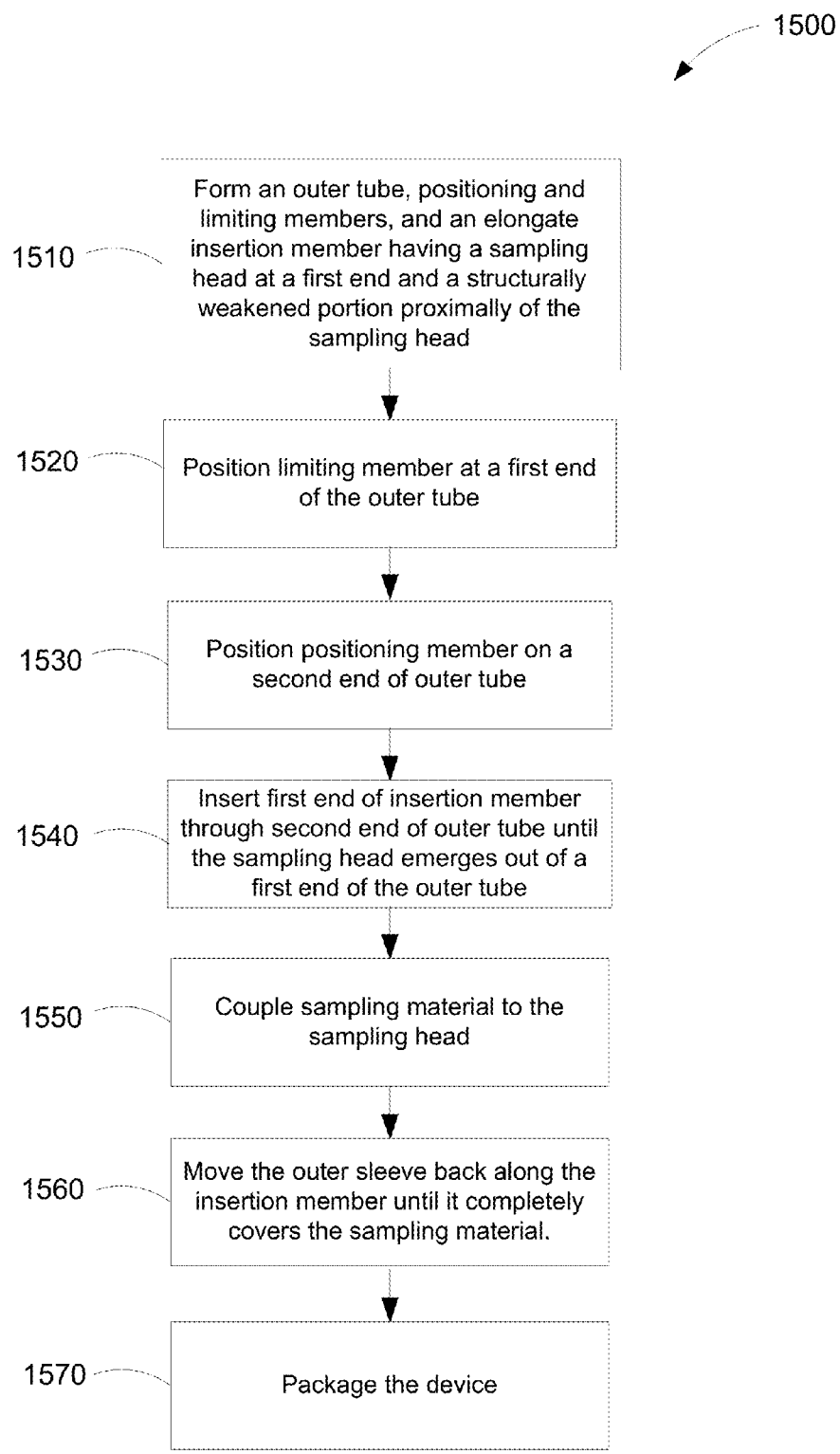
FIG. 15 is a flowchart of a method of manufacturing and assembling the device of FIG. 4.

The method of manufacturing and assembling the device of some embodiments is shown in FIG. 15. At 1510, the outer tube, positioning and limiting members, and insertion member are formed. The insertion member is formed to have a sampling head at one end, and a structurally weakened portion 20 proximally of the sampling head.

The first step in the assembly may be to position positioning member 11 onto outer sleeve 10 at 1520, aligning this with one of longitudinal markings 15. In some embodiments, positioning member 11 may be aligned with longitudinal markings 15 corresponding to a measurement of 50 mm. At 1530, the next step may be to position limiting member 12 onto outer sleeve 10 at the end opposite to longitudinal markings 11. Limiting member 12 should be pushed onto the appropriate end of outer sleeve 10 until that end of outer sleeve 10 aligns with ridge 24, which can be detected through visual inspection or, in embodiments that have a corresponding internal positioning ridge, tactile feedback.

Elongate insertion member 4 may then be inserted into outer sleeve 10 at 1540. First end 5 of elongate insertion member 4 is inserted into outer sleeve 10 at the end on which limiting member 12 is positioned. Elongate insertion member 4 is inserted until limiting member 12 receives shoulder portion 8. This will expose hook 30 and structurally weakened portion 20 out of the distal end of outer tube 10 (that does not have limiting member 12 positioned on it).

The next step may be to assemble sampling material 14 onto hook 30 at 1550. In some embodiments, a length of sampling material 14 is selected and folded. In some embodiments, this may be folded into 2 or 4 equal sections and one end trimmed to provide four free ends. Sampling material 14 may be slightly compressed by the application of manual force, and inserted through opening 19 into slot 18 of hook 30. Sampling material 14 may then be further compressed, and in some embodiments the ends of sampling material 14 may be trimmed to ensure that they are all the same length.

Outer sleeve 10 is then moved back along elongate insertion member 4 at 1560, disengaging limiting member 12 from shoulder portion 8. Outer sleeve 10 should be positioned such that it completely covers sampling material 14. In some embodiments, the end of outer sleeve 10 will be positioned at a maximum of 2 mm away from the ends of sampling material 14. Outer sleeve 10 should not be turned or twisted relative to elongate insertion member 4 while being positioned, to avoid twisting or tangling sampling material 14.

Sampling device 1 may then be packaged in a sterile pouch at 1570, which may be a sterile peel pouch, and sealed. The entire product may then be sterilized and labelled. In some embodiments, sampling device 1 may be assembled into or sold as part of a kit with other devices, such as a container comprising a post-sampling transport medium, a severing device such as a blade or scissors, or additional sampling devices such as a blood sampling kit.

Once intact fetal cells or cffDNA is obtained, the sample can be stored at 0 to 4° C. until use to minimize the number of dead cells, cell debris and cell clumps. The sample can be transported and/or stored in HypoThermosol-FRS (HTS-FRS) Medium (Biolife Solutions) at 4° C. For long term storage, the sample can be stored in CryoStor CS5 (Biolife Solutions) at −80° C.

In a further embodiment, the sample is transported and/or stored in Gibco™ 10 AmnioMaxII, Gibco™ AmnioMax C-100, or Gibco™ Keratinocyte-SFM supplemented with 2% fetal bovine serum, heparin (2500 U), hydrocortisone (5 µg/ml), insulin (5 µg/ml), human epidermal growth factor (5 µg/ml), human basic fibroblast growth factor (5 µg/ml), 25 µg/ml gentamycin, 50 ng/ml amphotericin B, 1-2 mmol/L vitamin C (ascorbic acid) or a water soluble analogue of vitamin E (1 mmol/L Trolox). Alternatively, the sample is fixed in alcohol or liquid-based cytology medium; for example "Universal Collection Medium" supplied by Digene Corp. as described in U.S. Pat. No. 6,969,585.

In one embodiment, the transport and/or storage media comprises serum such as bovine calf serum or human serum.

For short term storage, for example a few hours, phosphate buffered saline (PBS) is sufficient. In some embodiments, Dulbecco's phosphate buffered saline (DPBS) by from Life Technologies may be used, which contains no calcium or magnesium. In a further embodiment, the storage medium is degassed with nitrogen to reduce oxidative stress to the samples.

Processing

In an embodiment, the sampling material 14 is carefully removed from the sampling head 9 using sterile forceps and placed back into the transport media or PBS, which in some embodiments may be DPBS. The sampling material 14 is washed with the original transport media or PBS present in the transport container. The sampling material 14 is washed by gently agitation (up & down motions). Further washes in PBS are used to remove the mucus/cells from the sampling material 14. This step maybe repeated a few times until the sampling material 14 is completely washed, or there is no evidence of mucus or cells being present on the sampling material 14. A total of 16-20 ml of sample is collected which comprises of cells, free nuclei, free nucleic acids, miRNAs, PBS and transport media.

In a further embodiment, red blood cells are removed from the sample. Red blood cells can be removed using any technique known in the art. Red blood cells (erythrocytes) may be depleted by, for example, density gradient centrifugation over Percoll, Ficoll, or other suitable gradients. Red blood cells may also be depleted by selective lysis using commercially available lysing solutions. For example, BD FACS lysing solution, Miltneyi Biotec's red blood cell lysis solution, Ammonium Chloride based lysing solutions (eg. STEMCELL™ Technologies) or other osmotic lysing agents may be used.

In some instances it is not necessary that intact cells be used for fetal material analysis. In these circumstances it is not essential that steps be taken to keep at least some of the cells alive. For example, the sample, or a portion thereof, can be snap frozen.

Labelling and/or Detection of Fetal Cells

Fetal cells can be positively and/or negatively selected using a variety of techniques well known in the art, including cell sorting, especially fluorescence activated cell sorting (FACS), by using an affinity reagent bound to a substrate (e.g., a plastic surface, as in panning), or by using an affinity reagent bound to a solid phase particle which can be isolated on the basis of the properties of the solid phase particles for example beads (e.g., coloured latex beads or magnetic particles). Naturally, the procedure used will depend on whether maternal or fetal cells are being selected and how the cells have been labelled.

For selection of cells by cell sorting, the cells are labelled directly or indirectly with a substance which can be detected by a cell sorter, preferably a dye. Preferably, the dye is a fluorescent dye. A large number of different dyes are known in the art, including fluorescein, rhodamine, Texas red, phycoerythrin, and the like. Any detectable substance which has the appropriate characteristics for the cell sorter may be used (e.g., in the case of a fluorescent dye, a dye which can be excited by the sorter's light source, and an emission spectra which can be detected by the cell sorter's detectors).

In flow cytometry, a beam of laser light is projected through a liquid stream that contains cells, or other particles, which when struck by the focussed light give out signals which are picked up by detectors. These signals are then converted for computer storage and data analysis, and can provide information about various cellular properties. Cells labelled with a suitable dye are excited by the laser beam, and emit light at characteristic wavelengths. This emitted light is picked up by detectors, and these analogue signals are converted to digital signals, allowing for their storage, analysis and display.

Many larger flow cytometers are also "cell sorters", such as FACS, and are instruments which have the ability to selectively deposit cells from particular populations into tubes, or other collection vessels. In a particularly preferred embodiment, the cells are isolated using FACS. This procedure is well known in the art and described by, for example, Melamed, et al. Flow Cytometry and Sorting Wiley-Liss, Inc., New York, N.Y. (1990); Shapiro Practical Flow Cytometry, 4 ed, Wiley-Liss, Hoboken, N.J. (2003); and Robinson et al. Handbook of Flow Cytometry Methods Wiley-Liss, New York, N.Y. (1993).

The cells can automatically be deposited in collection vessels as single cells or as a plurality of cells, e.g. using a laser, e.g. an argon laser (488 nm) and for example with a Flow Cytometer fitted with an Autoclone unit (Coulter EPICS Altra, Beckman21 Coulter, Miami, Fla., USA). Other examples of suitable FACS machines useful for the methods of the invention include, but are not limited to, MoFlo™ High-speed cell sorter (Dako-Cytomation Ltd), FACS Aria™ (Becton Dickinson), ALTRA™ Hyper sort (Beckman Coulter) and CyFlow™ sorting system (Partec GmbH).

For the selection of cells from a sample using solid-phase particles, any particle with the desired properties may be utilized. For example, large particles (e.g., greater than about 90-100 nm in diameter) may be used to facilitate sedimentation. Preferably, the particles are "magnetic particles" (i.e., particles which can be collected using a magnetic field). Typically, maternal cells labeled with the magnetic probe are passed through a column, held within a magnetic field. Labeled cells are retained in the column (held by the magnetic field), whilst unlabeled cells pass straight through and are eluted at the other end. Magnetic particles are now commonly available from a variety of manufacturers including Dynal Biotech (Oslo, Norway) and Miltenyi Biotech GmbH (Germany). An example of magnetic cell sorting (MACS) is provided by Al-Mufti et al. (1999) and U.S. Pat. No. 4,675,286.

Laser-capture microdissection (LCM) can also be used to select labelled cells or cells based on morphology. Methods of using laser-capture microdissection are known in the art (see, for example, U.S. 20030227611 and Bauer et al., 2002).

As the skilled person will appreciate, maternal cells can be labelled with one type of label, and fetal cells with another type of label, and the respective cells types selected on the basis of the different labelling. For example, maternal cells can be labelled as described herein such that they produce a fluorescent green signal, and maternal cells can be labelled as described herein such that they produce a fluorescent red signal.

Following enrichment, the cells can be cultured in vitro to expand fetal cells numbers using techniques known in the art. For example culturing in RPMI 1640 media (Gibco) may be used.

Enrichment/Separation of Extracellular Nucleic Acids in the Sample

Free nucleic acids in the sample obtained using the described methods and devices are enriched/separated from at least 10%, more preferably at least 20%, more preferably at least 30%, more preferably at least 40%, more preferably at least 50%, more preferably 60%, more preferably 70%, more preferably 80%, more preferably 90%, more preferably 95%, more preferably 99%, and most preferably all of the cells and nuclei in the original sample taken from the female. This can be achieved using methods known in the art for separating free nucleic acids from intact cells/nuclei. For example, in one embodiment the sample is centrifuged at about 4,000 to 7,000 g for 5 to 10 minutes, and the supernatant comprising the nucleic acids is aspirated from the pellet comprising cells. This procedure may be repeated to minimize the number of cells in the enriched sample.

Methods of nucleic acid extraction are known in the art. In one embodiment, this is achieved by using a protocol based on extraction using organic solvents such as a mixture of phenol and chloroform, followed by precipitation with ethanol (see, for example, J. Sambrook et al., "Molecular Cloning: A Laboratory Manual", 1989, 2nd Ed., Cold Spring Harbour Laboratory Press: New York, N.Y.) or Triton/Heat/Pheno protocol (THP). Other methods include but are not limited to: salting out DNA extraction; trimethylammonium bromide salt DNA extraction; gelatine extraction; silica, glass bead, or diatom extraction; guanidinium thiocyanate acidphenol based extraction; guanidine-hydrochloride based extraction; guanidinium thiocyanate extraction; and methods using centrifugation through cesium chloride or similar gradients. There are also numerous kits/various protocols that have emerged and can be used to extract cell free nucleic acids from body fluids such as plasma/serum/urine that are commercially available, for example, QIAamp DNA Blood Mini Kit, QIAamp DSP Virus Kit, QIAamp UltraSens Virus Kit QIAamp Circulating Nucleic Acid, QIAamp DNA Blood Maxi Kit, QIAamp MiniElute Virus Spin Kit, RNeasy Mini Kit combined with TRIzol LS reagent, QIAsymphony DSP Virus/Pathogen Midi Kit, (from Qiagen Inc., Valencia, Calif., USA), High Pure PCR Template Preparation kit, MagNA Pure LC DNA Isolation Kit—Large Volume, MagNA Pure Compact Nucleic Acid Isolation Kit I—Large Volume (from Roche Diagnostics, Indianapolis, Ind., USA), NucliSENS® easyMAG®, NucliSENS® miniMAG® (from bioMerieux Inc., Hazelwood, Mo., USA), NucleoSpin Plasma XS Kit (from Macherey-Nagel GmbH & Co, KG, Düren, Germany), Wizard® Plus Minipreps DNA Purification System (from Promega Co, Madison, Wis. USA), Plasma/Serum Circulating DNA Purification Kit (Norgen Biotek Co. Thorold, ON Canada), SnoMag™ Circulating DNA Kit (Snova Biotechnologies Co, Warren, N.J. USA), FitAmp Circulating DNA Quantification Kit (Epigentek Group Inc. n Farmingdale, N.Y. USA), Circulating DNA Plus extraction kit (BioSamPle Solutions LLC, Bethlehem, Pa. USA), magnetic bead separation method, and magnetic capture hybridization (MCH) method. Recently, along these extraction kits, several new automated robotic systems have also been designed, which are commercially available from, for example Qiagen Inc. (Valencia, Calif., USA) (QIAsymphony SPED), Roche Diagnostics GmbH (Mannheim, Germany) (MagNA Pure™ LC Instrument).

Uses

Free fetal nucleic acids, fetal cells, free fetal nuclei and/or miRNAs obtained using the methods described can be analyzed for traits of interest and/or abnormalities of the fetus using techniques known in the art. Traits of interest may give indications of conditions such as pre-eclampsia and preterm labour, among other conditions. Such analysis can be performed on any cellular/nuclear/molecular material that enables the trait, or predisposition thereto, to be detected.

In one preferred embodiment, chromosomal abnormalities are detected. By "chromosomal abnormality" we include any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes which include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome, haemophilia, spinal muscular dystrophy, myotonic dystrophy, Menkes disease and neurofibromatosis, which can be detected by DNA analysis.

The phrase "genetic abnormality" also refers to a single nucleotide substitution, deletion, insertion, micro-deletion, micro-insertion, short deletion, short insertion, multinucleotide substitution, and abnormal DNA methylation and loss of imprint (LOI). Such a genetic abnormality can be related to an inherited genetic disease such as a single-gene disorder (e.g., cystic fibrosis, Canavan, Tay-Sachs disease, Gaucher disease, Familial Dysautonomia, Niemann-Pick disease, Fanconi anemia, Ataxia telengectasia, Bloom syndrome, Familial Mediterranean fever (FMF), X-linked spondyloepiphyseal dysplasia tarda, factor XI), an imprinting disorder [e.g., Angelman Syndrome, Prader-Willi Syndrome, Beckwith-Wiedemann syndrome, Myoclonus dystonia syndrome (MDS)], or to predisposition to various diseases (e.g., mutations in the BRCA1 and BRCA2 genes). Other genetic disorders which can be detected by DNA analysis are known such as thalassaemia, Duchenne muscular dystrophy, connexin 26, congenital adrenal hypoplasia, X-linked hydrocephalus, ornithine transcarbamylase deficiency, Huntington's disease, mitochondrial disorder, mucopolysaccharidosis I or IV, Norrie's disease, Rett syndrome, Smith-Lemli Optiz syndrome, 21-hydroxylase deficiency or holocarboxylase synthetase deficiency, diastrophic dysplasia, galactosialidosis, gangliosidosis, hereditary sensory neuropathy, hypogammaglobulinaemia, hypophosphatasia, Leigh's syndrome, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 8th Edition, Volumes I, II, III and IV, Scriver, C. R. et al. (eds), McGraw Hill, 2001. Clearly, any genetic disease where the gene has been cloned and mutations detected can be analyzed.

The methods can also be used to determine the sex of the fetus. For example, fetal DNA can be analyzed with Y-chromosome specific markers.

In yet another use, the methods described herein can be used for paternity testing. Where the paternity of a child is disputed, the procedures enable this issue to be resolved early on during pregnancy. Many procedures have been described for parentage testing which rely on the analysis of suitable polymorphic markers. As used herein, the phrase "polymorphic markers" refers to any nucleic acid change (e.g., substitution, deletion, insertion, inversion), variable number of tandem repeats (VNTR), short tandem repeats (STR), minisatellite variant repeats (MVR), single nucleotide polymorphisms (SNPs) and the like. Typically, parentage testing involves DNA fingerprinting targeting informative repeat regions, or the analysis of highly polymorphic regions of the genome such as HLA loci.

The methods can also be used for diagnosing, monitoring, or predicting pre-eclampsia in a pregnant woman. The term "pre-eclampsia" as used herein refers to a condition that occurs during pregnancy, the main symptom of which is various forms of high blood pressure often accompanied by the presence of proteins in the urine and edema (swelling). Pre-eclampsia, sometimes called toxemia of pregnancy, is related to a more serious disorder called "eclampsia," which is preeclampsia together with seizure. These conditions usually develop during the second half of pregnancy (after 20 weeks), though they may develop shortly after birth or before 20 weeks of pregnancy. Cell free fetal nucleic acids or miRNAs can be used as a potential biomarker for identifying subjects at risk of developing pre-eclampsia using techniques described in the art. The abundance of trophoblast cells in the transcervical canal number can also be used as a predictor of pre-eclampsia.

In yet another use, the methods described herein can be used for diagnosis, monitoring, or predicting pre-term labor in a pregnant woman. The term "pre-term labor" as used herein refers to the condition where labor that begins more than three weeks before the full gestation period of about 40 weeks, which often leads to premature birth if not treated. The levels of cell free fetal nucleic acids or miRNAs can be used as an indicator of pre-term labor/pre-term delivery using techniques described in the art, such as by determining when there are high levels of cell free fetal DNA, which indicates increased risk of these conditions.

Analysis of Extracellular Fetal Nucleic Acids or Enriched/Isolated Fetal Cells

Figure 12:
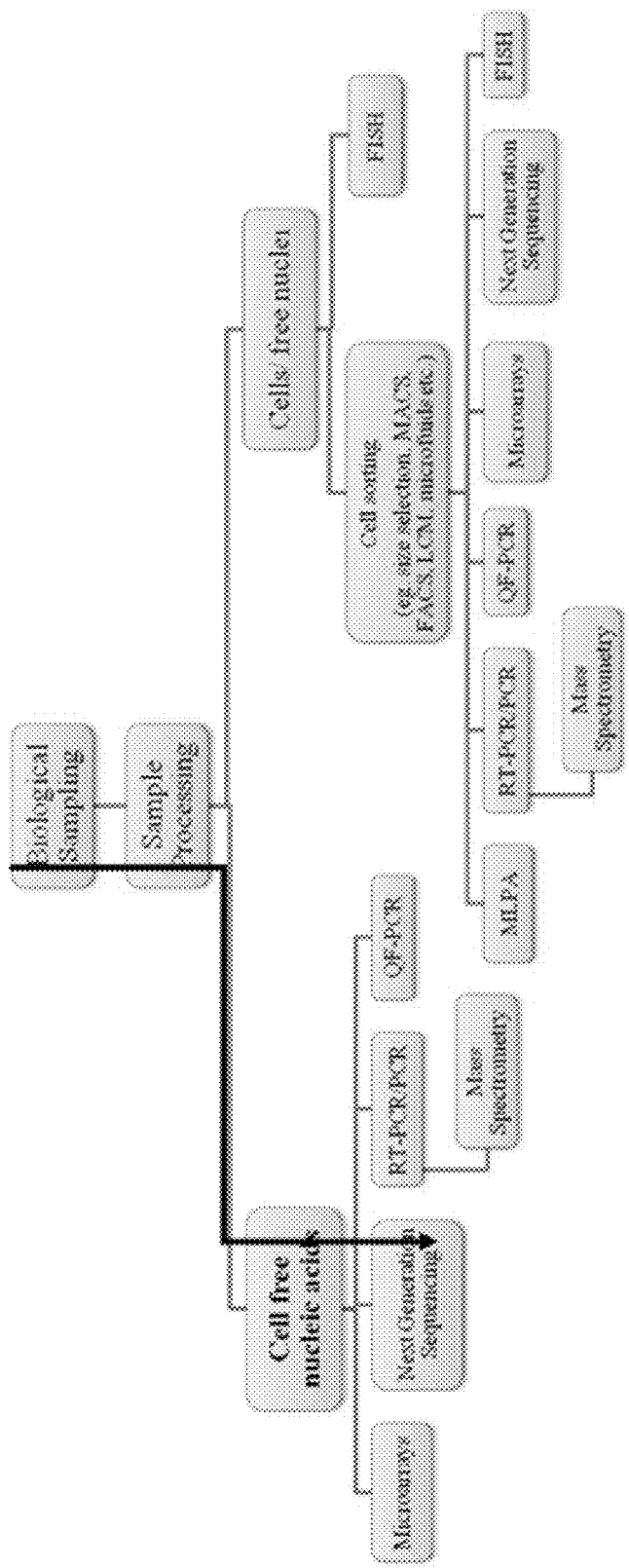
FIG. 12 is a flowchart showing an example of analytical methods which can be employed on extracellular nucleic acid samples obtained with the sampling device of FIG. 4.
Figure 13:
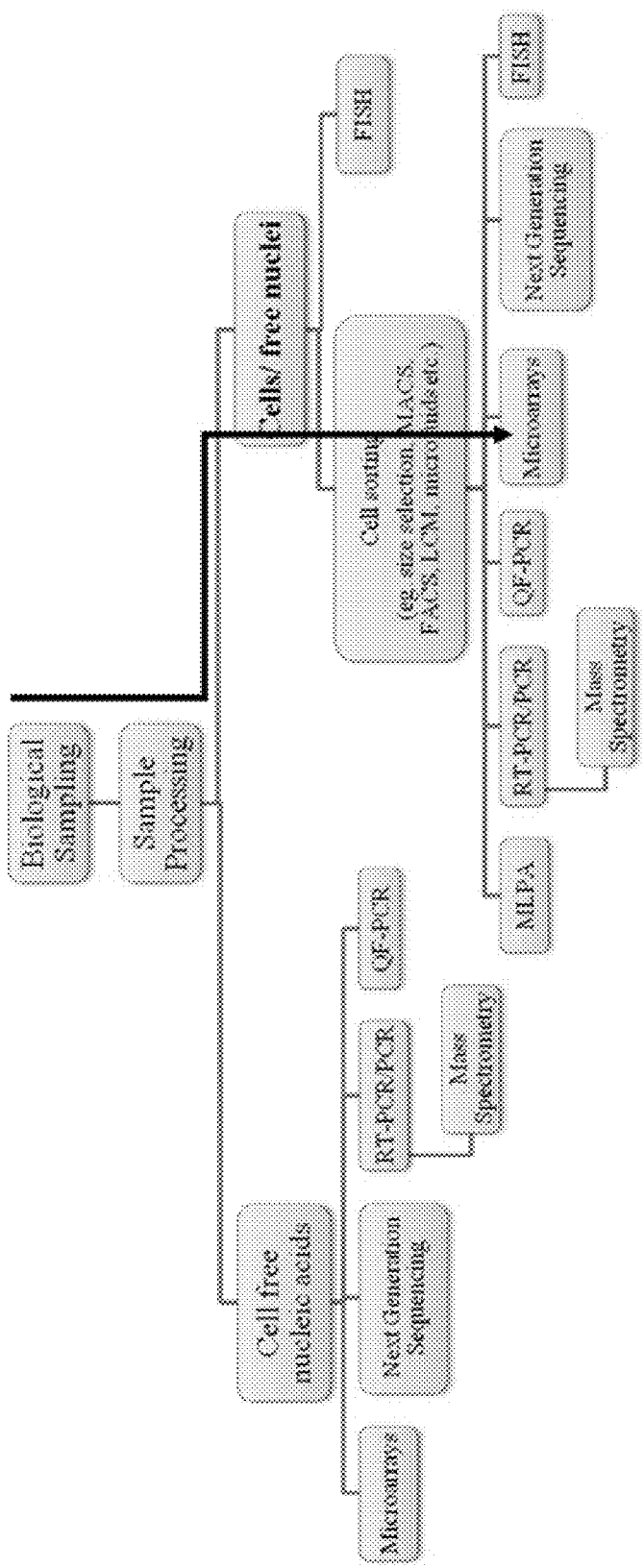
FIG. 13 is a flowchart showing an example of analytical methods which can be employed on enriched/isolated fetal cells obtained with the sampling device of FIG. 4.

Free fetal nucleic acids, enriched/isolated fetal cells, free fetal nuclei and/or miRNAs obtained using the methods described can be analyzed by a variety of procedures, however, typically genetic assays will be performed as shown in FIGS. 12 and 13. Genetic assay methods include the standard techniques of karyotyping, analysis of methylation patterns, restriction fragment length polymorphism (RFLP) assays, next generation sequencing (NGS) (also known as massively parallel sequencing (MPS) and PCR-based assays (including quantitative fluorescent polymerase chain reaction (QF-PCR) STR analysis, whole genome amplification and microarray analysis), as well as other methods described below.

Chromosomal abnormalities, either in structure or number, can be detected by karyotyping which is known in the art such as FISH. Karyotyping analysis is generally performed on cells which have been arrested during mitosis by the addition of a mitotic spindle inhibitor such as colchicine. Preferably, a Giemsa-stained chromosome spread is prepared, allowing analysis of chromosome number as well as detection of chromosomal translocations.

The acronym "FISH" references a technique that uses chromophore tags (fluorophores) that emit a secondary signal if illuminated with an excitation light to detect a chromosomal structure. FISH uses fluorescent probes which bind only to those parts of the chromosome with which they show a high degree of sequence similarity. Such tags may be directed to specific chromosomes and specific chromosome regions. The probe has to be long enough to hybridize specifically to its target (and not to similar sequences in the genome), but not too large to impede the hybridization process, and it should be tagged directly with fluorophores. This can be done in various ways, for example nick translation or PCR using tagged nucleotides. If signal amplification is necessary to exceed the detection threshold of the microscope (which depends on many factors such as probe labelling efficiency, the kind of probe and the fluorescent dye), secondary fluorescent tagged antibodies or streptavidin are bound to the tag molecules, thus amplifying the signal.

The genetic assays may involve any suitable method for identifying mutations or polymorphisms, such as: sequencing of the DNA at one or more of the relevant positions; differential hybridization of an oligonucleotide probe designed to hybridize at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP assays; selective DNA amplification using oligonucleotides which are matched for the wild type sequence and unmatched for the mutant sequence or vice versa; or the selective introduction of a restriction site using a PCR (or similar) primer matched for the wild-type or mutant genotype, followed by a restriction digest. The assay may be indirect, i.e. capable of detecting a mutation at another position or gene which is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the PCR method and modifications thereof.

Amplification of free fetal nucleic acids, DNA from enriched/isolated fetal cells, free fetal nuclei and/or miRNAs may be achieved by the established PCR methods or by developments thereof or alternatives such as quantitative PCR, QF-PCR, multiplex fluorescent polymerase chain reaction (MF-PCR), multiplex ligation dependent probe amplification (MLPA), digital PCR, real time polymerase chain reaction (RT-PCR), methylated DNA immunoprecipitation real-time quantitative polymerase chain reaction (MeDIP RT-PCR), single cell PCR, ice-COLD PCR, whole genome amplification, microarray analysis, polymerase chain reaction restriction fragment length polymorphism (PCR-RFLP), real time polymerase chain reaction restriction fragment length polymorphism (RT-PCR-RFLP), hot start PCR, nested PCR, in situ polonony PCR, in situ rolling circle amplification (RCA), bridge PCR, picotiter PCR and emulsion PCR. Other suitable amplification methods include the ligase chain reaction (LCR), quantitative reverse transcription-polymerase chain reaction (qRT-PCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

Free fetal nucleic acids, DNA from enriched/isolated fetal cells and/or free fetal nuclei obtained using the methods described can also be analyzed using commercial platforms such as the SEQureDx™ technology incorporating massively parallel shotgun sequencing (MPSS) (Seqeunom Inc., San Deigo, Calif., USA), MPS using SAFeR algorithm (Verinata Health, Redwood City, Calif., USA), Digital ANalysis of Selected Regions (DANSR™) technology incorporating targeted sequencing and Fetal-fraction Optimized Risk of Trisomy Evaluation (FORTE™) algorithm (Ariosa Diagnostics Inc., San Jose, Calif., USA) and next generation SNP-based targeted aneuploidy testing (Natera Inc., San Carlos, Calif., USA).

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Variations and/or modifications may be made to the above-described embodiments, without departing from the broad general scope of the present disclosure. The present embodiments are, therefore, to be considered in all respects as illustrative and not restrictive.

The invention claimed is:

1. A sampling device adapted for transcervical sampling of biological materials from a patient comprising:
   an outer tube having visible reference marks at a first end of the tube, the marks indicating intervals of distance along the first end of the tube;
   an elongate insertion member having a first end and a second end, wherein the first end is distal of the second end, the insertion member being received in and sized to be movable through the outer tube;
   a coupling portion disposed at the first end of the insertion member;
   a sampling portion coupled to the coupling portion and configured to collect the biological materials by absorption or adsorption;

a first stop disposed adjacent the reference marks on the outer tube, the position of the first stop being adjustable with respect to the reference marks on the outer tube; and a second stop arranged to restrict the distance that the first end of the insertion member can extend past the first end of the outer tube;

wherein the first stop is sized to pass through a vagina of the patient but to be restricted from passing through an external os of a cervix of the patient, and wherein the outer tube is sized to pass through the external os; and wherein the insertion member is formed to have a structurally weakened portion that is structurally weakened relative to immediately adjacent portions of the insertion member and is formed proximally of the coupling portion at the first end of the insertion member, wherein the structurally weakened portion facilitates separation of the coupling portion from the insertion member; and wherein the outer tube and insertion member are movable relative to each other between at least a first position where the sampling portion is covered by the outer tube, a second position where the sampling member is uncovered by the outer tube and the coupling portion is at least partially covered by the outer tube, and a third position where the sampling portion, coupling portion and structurally weakened portion are uncovered by the outer tube to allow separation of the coupling portion from the insertion member.

2. The device of claim 1, wherein the movement of the outer tube with respect to the elongate insertion member from the first position to the third position is limited by the second stop contacting a limiting structure that restrains the outer tube in the second position until the second stop overcomes the limiting structure.

3. The device of claim 2 wherein the limiting structure is a circumferentially enlarged portion of the insertion member and the second stop is a tubular member, the tubular member being able to overcome the limiting structure by receiving the limiting structure within a portion of a central lumen, and the limiting member having an interference fit with the second stop.

4. The device of claim 1, wherein the structurally weakened portion is arranged such that when a moment is applied about the structurally weakened portion, plastic deformation or breaking of the insertion member tends to occur at the weakened portion.

5. The device of claim 1, wherein a structural weakening of the structurally weakened portion is highly localized.

6. The sampling device of claim 1, wherein the reference marks on the outer tube allow the distance between the position of the first stop and the first end of the tube to be determined.

7. The sampling device of claim 1, wherein the first stop is adjustable to a position that allows the sampling portion of the insertion member to be positioned at the internal os of the patient when the first stop is abutting the external os of the patient and the insertion member has been moved through the outer tube until the second stop has been engaged.

8. The sampling device of claim 1, wherein the coupling portion comprises a hook and the sampling portion is retained in the first end of the insertion member by being inserted into an opening of the hook.

9. The sampling device of claim 8, wherein the opening of the hook is covered by the outer tube when the outer tube is in the first and second positions, and wherein the opening of the hook is uncovered by the outer tube when the outer tube is in the third position.

10. The sampling device of claim 1, wherein the sampling portion comprises a sponge material.

11. The sampling device of claim 10, wherein the sponge material comprises a multi-filamentous array of sponge fingers.

12. The sampling device of claim 1, wherein the sponge material is polyvinyl acetal.

13. The sampling device of claim 1, wherein the sampling portion comprises a material adapted to expand upon absorption of the biological materials from a dry compressed state to a swollen state.

14. The sampling device of claim 1 wherein the insertion member is curved along a long dimension of the insertion member.

15. The sampling device of claim 1 wherein the sampling material is configured to collect any one or more of:
cell-free nucleic acids (DNA and RNA);
miRNAs;
protein;
cell free fetal nucleic acids (DNA/RNA);
fetal cells;
free fetal nuclei;
sperm;
viruses;
bacteria;
nuclear material;
cellular material; and
molecular material.

16. A sampling device adapted for transcervical sampling of biological materials from a patient comprising:
an outer tube having visible reference marks at a first end of the tube, the marks indicating intervals of distance along the first end of the tube;
an elongate insertion member having a first end and a second end, wherein the first end is distal of the second end, the insertion member being received in and sized to be movable through the outer tube;
a coupling portion disposed at the first end of the insertion member;
a sampling portion coupled to the coupling portion and configured to collect the biological materials by absorption or adsorption;
a first stop disposed adjacent the reference marks on the outer tube, the position of the first stop being adjustable with respect to the reference marks on the outer tube; and
a second stop arranged to restrict the distance that the first end of the insertion member can extend past the first end of the outer tube;
wherein the first stop is sized to pass through a vagina of the patient but to be restricted from passing through an external os of a cervix of the patient, and wherein the outer tube is sized to pass through the external os; and
wherein the insertion member is formed to have a structurally weakened portion that is structurally weakened relative to immediately adjacent portions of the insertion member and is formed proximally of the coupling portion at the first end of the insertion member, wherein the structurally weakened portion facilitates separation of the coupling portion from the insertion member.

17. A kit for transcervical sampling of biological materials from a patient comprising:
the sampling device of claim 1;
a severing member actuable to separate the coupling and sampling portions from the insertion member; and
a transport medium to transport the coupling and sampling portions after they have been severed from the insertion member.

18. A kit for transcervical sampling of biological materials from a patient comprising:
   the sampling device of claim 16;
   a severing member actuable to separate the coupling and sampling portions from the insertion member; and
   a transport medium to transport the coupling and sampling portions after they have been severed from the insertion member.

* * * * *